US008211861B2

(12) United States Patent
Serra

(10) Patent No.: US 8,211,861 B2
(45) Date of Patent: *Jul. 3, 2012

(54) COMPOSITIONS FOR AND METHODS OF ENHANCING THE IMMUNE RESPONSE TO ANTIGENS

(75) Inventor: Vincent Serra, Bondoufle (FR)

(73) Assignee: Wittycell, Reims (FR)

(*) Notice: Subject to any disclaimer, the term of this patent is extended or adjusted under 35 U.S.C. 154(b) by 0 days.

This patent is subject to a terminal disclaimer.

(21) Appl. No.: 12/746,488

(22) PCT Filed: Dec. 5, 2008

(86) PCT No.: PCT/IB2008/003945
§ 371 (c)(1),
(2), (4) Date: Dec. 5, 2008

(87) PCT Pub. No.: WO2009/101475
PCT Pub. Date: Aug. 20, 2009

(65) Prior Publication Data
US 2010/0322952 A1  Dec. 23, 2010

Related U.S. Application Data

(60) Provisional application No. 60/992,460, filed on Dec. 5, 2007.

(51) Int. Cl.
*A61K 39/00* (2006.01)
*A61K 38/17* (2006.01)
*C07H 15/04* (2006.01)
(52) U.S. Cl. .................. 514/25; 536/17.9; 424/184.1
(58) Field of Classification Search .................. None
See application file for complete search history.

(56) References Cited

U.S. PATENT DOCUMENTS

| | | | |
|---|---|---|---|
| 5,242,800 A | 9/1993 | Jimenez et al. | |
| 5,604,207 A | 2/1997 | DeFrees et al. | |
| 5,767,092 A | 6/1998 | Koezuka et al. | |
| 5,780,441 A | 7/1998 | Higa et al. | |
| 5,785,975 A | 7/1998 | Parikh | |
| 5,849,716 A | 12/1998 | Akimoto et al. | |
| 5,936,076 A | 8/1999 | Higa et al. | |
| 5,958,426 A | 9/1999 | Moreau et al. | |
| 6,071,884 A | 6/2000 | Koezuka et al. | |
| 6,417,167 B1 | 7/2002 | Maruyama et al. | |
| 6,531,453 B1 | 3/2003 | Taniguchi et al. | |
| 6,610,835 B1 | 8/2003 | Liotta et al. | |
| 6,635,622 B2 | 10/2003 | Tomiyama et al. | |
| 6,747,010 B2 | 6/2004 | Taniguchi et al. | |
| 7,273,852 B2 | 9/2007 | Tsuji et al. | |
| 7,273,853 B2 | 9/2007 | Or et al. | |
| 7,645,873 B2 | 1/2010 | Savage et al. | |
| 7,989,423 B2 | 8/2011 | Savage et al. | |
| 2002/0115624 A1 | 8/2002 | Behar et al. | |
| 2003/0139351 A1 | 7/2003 | Taniguchi et al. | |
| 2003/0153514 A1 | 8/2003 | Yagita | |
| 2003/0157135 A1 | 8/2003 | Tsuji et al. | |
| 2004/0127429 A1 | 7/2004 | Tsuji | |
| 2004/0166554 A1 | 8/2004 | Chamoles | |
| 2004/0266726 A1 | 12/2004 | Yagita | |
| 2005/0192248 A1 | 9/2005 | Tsuji et al. | |
| 2005/0222048 A1 | 10/2005 | Tsuji et al. | |
| 2006/0019246 A1 | 1/2006 | Tsuji et al. | |
| 2006/0073118 A1 | 4/2006 | Bendelac et al. | |
| 2006/0211856 A1 | 9/2006 | Tsuji et al. | |
| 2008/0095787 A1 | 4/2008 | Teyton | |
| 2008/0279894 A1 | 11/2008 | Teyton et al. | |
| 2009/0047299 A1* | 2/2009 | Savage et al. ............ 424/184.1 |

FOREIGN PATENT DOCUMENTS

| | | |
|---|---|---|
| EP | 0988860 | 3/2000 |
| EP | 1016409 | 7/2000 |
| WO | WO 99/33475 | 7/1999 |
| WO | WO 03/009812 | 2/2003 |
| WO | WO 03/018039 | 3/2003 |
| WO | WO 03/105769 | 12/2003 |
| WO | WO 2005/000348 | 1/2005 |
| WO | WO 2005/102049 | 11/2005 |
| WO | WO 2006/029010 | 3/2006 |
| WO | WO 2006/083671 | 8/2006 |
| WO | WO 2007/007946 | 1/2007 |
| WO | WO 2007/050668 | 5/2007 |
| WO | WO 2007/118234 | 10/2007 |
| WO | WO 2007/126163 | 11/2007 |
| WO | WO 2008/005824 | 1/2008 |
| WO | WO 2008/080926 | 7/2008 |
| WO | WO 2008/082156 | 7/2008 |
| WO | WO 2009/060086 | 5/2009 |
| WO | WO 2010/023498 | 3/2010 |

OTHER PUBLICATIONS

Liu et al. "A modified α-galactosyl ceramide for staining and stumulating natural killer T cells," *J. of Immunological Methods*, vol. 312. 2006. pp. 34-39.

Long et al. "Synthesis and evaluation of stimulatory properties of *Sphingomondadaceae* glycolipids." *Nature Chem. Bio.* vol. 3. No. 9. 2007. pp. 559-564.

Ando et al., "Solid-phase capture-release strategy applied to oligosaccharide synthesis on a soluble polymer support," *Agnew. Chem. Int. Ed.* (2001) 40:4725-4728.

Beaudoin, L. et al., "NKT cells inhibit the onset of diabetes by impairing the development of pathogenic T cells specific for pancreatic beta cells," *Immunity* (2002) 17:725-736.

(Continued)

*Primary Examiner* — Traviss C McIntosh, III
(74) *Attorney, Agent, or Firm* — Merchant & Gould P.C.

(57) ABSTRACT

Compositions comprising the compound of formula are provided herein. Also provided are methods of enhancing an immune response of a subject to an antigen by administering the antigen and the composition. The enhanced immune response may be an humoral immune response, a CD4+ T cell response, a CD8+ T cell response or result in activation of antigen presenting cells. Methods of enhancing the immune response by intramuscular administration of an antigen and the composition including the compound of formula I are also provided.

27 Claims, 16 Drawing Sheets

OTHER PUBLICATIONS

Bendelac et al., "Increased interleukin 4 and immunoglobulin E production in transgenic mice overexpressing NK1 T cells," *J. Exp. Med.* (1996) 184: 1285-1293.

Bendelac, A. et al., "Autoreactivity by design: innate B and T lymphocytes," 1:177-186. *Natur. Rev. Immunol.* (2001) 1:177-186.

Bendelac, A. et al., "The biology of NKT cells," *Ann. Rev. Immunol.* (2007) 25:297-336.

Bendelac, A., "Nondeletional pathways for the development of autoreactive thymocytes," *Nat. Immunol.* (2004) 5:557-558.

Benlagha, K. et al., "In vivo identification of glycolipid antigen-specific T cells using fluorescent CD1d tetramers," *J. Exp. Med.* (2000) 191:1895-1903.

Brigl et al., "Mechanism of CDId-restricted natural killer T cell activation during microbial infection," *Nat. Immunol.* (2003) 4: 1230-1237.

Brigl et al., "T cell function and antigen presentation," *Annu. Rev. Immunol.* (2004) 22: 817-890.

Brossay, L. et al., "Cutting edge: structural requirements for galactosylceramide recognition by CD1-restricted NK T cells," *J. Immunol.* (1998) 161(10):5124-5128.

Brutkiewicz et al., "CD1d-mediated antigen presentation to natural killer T (NKT) cells," *Critical Reviews in Immunology* (2003) 23: 403-419.

Brutkiewicz et al., "Natural killer T (NKT) cells and their role in antitumor immunity," *Critical Reviews in Oncology/Hematology* (2002) 41: 287-298.

Cantu et al., "The paradox of immune molecular recognition of alpha-galactosylceramide; low affinity, low specificity for CD1d, high affinity for alpha beta TCRs," *J. Immunol.* (2003) 170: 4673-4682.

Corey et al., "A new method for the synthesis of organic nitro compounds," *J. Am. Chem. Soc.* (1984) 106:3682-3683.

Daoudi, J-M. et al., "New bicyclam-galcer analogue conjugates: synthesis and in vitro anti-HIV activity," *Biorg. Med. Chem. Lett.* (2004) 14:495-498.

Dascher, C.C. et al., "CD1 Antigen Presentation and Infectious Disease," *Contributions to Microbiology* (2003) 10:164-182.

Davis, N.J. et al., "Chemical Synthesis of Disaccharides Which are Partial Structures of the Glycosaminoglycan Heparan Sulfate," *J. Chem. Soc.* (1994) 1:359-368.

De Libero, G. et al., "Self glycosphingolipids: new antigens recognized by autoreactive T lymphocytes," *News Physiol. Sci.* (2003) 18:71-76.

Fischer, K. et al., "Mycobacterial phosphatidylinositol mannoside is a natural antigen for CD1d-restricted T cells," *Proc. Natl. Acad. Sci. USA* (2004) 101:10685-10690.

Fujii et al., "Activation of natural killer T cells by alpha-galactosylceramide rapidly induces the full maturation of dendritic cells in vivo and thereby acts as an adjuvant for combined CD4 and CD8 T cell immunity to a coadministered protein," *J. Exp. Med.* (2003) 198:267-279.

Garrity, G.M. et al., Taxonomic Outline of the Procaryotic Genera, Bergey's Manual of Systematic Bacteriology, 2nd Edition (Apr. 2001).

Godfrey, D.I. et al., "Going both ways: immune regulation via CD1d-dependent NKT cells," *J. Clin. Invest.* (2004) 114(10):1379-1388.

Godfrey, D.I. et al., "The elusive NKT cell antigen—is the search over?" *Science* (2004) 306:1687-1688.

Goff, R.D. et al., "Effects of lipid chain lengths in alpha-galactosylceramides on cytokine release by natural killer T cells," *J. Am. Chem. Soc.* (2004) 126:13602-13603.

Goodman & Gilman's The Pharmacological Basis of Therapeutics, Tenth Edition, Hardman and Limbird, editors, The McGraw-Hill Companies, Inc., New York, (2001) 54-56.

Gui, M. et al., "TCR beta chain influences but does not solely control autoreactivity of V alpha 14J281T cells," *J. Immunol.* (2001) 167(11):6239-6246.

Gumperz, J.E. et al., "Functional distinct subsets of CD1d-restricted natural killer T cells revealed by CD1d tetramer staining," *J. Exp. Med.* (2002) 195(5):625-636.

Gumperz, J.E. et al., "Murine CD1d-restricted T cell recognition of cellular lipids," *Immunity* (2000) 12:211-221.

Gupta, R.K. et al., "Adjuvants—a balance between toxicity and adjuvanticity," *Vaccine* (1993) 11(3):293-306.

Hashimoto, S. et al., "Glycosylation Using Glucopyranosyl Fluorides and Silicon-Based Catalysts, Solvent Dependency of the Stereoselection," *Tetrahedron Letters* (1984) 25:13:1379-1382.

Hayashi, M. et al., "Simple Synthesis of Glycosyl Fluorides," *Chem. Letters* (1984) 1747-1750.

Hermans, I.F. et al., "NKT cells enhance CD4+ and CD8+ T cell responses to soluble antigen in vivo through direct interaction with dendritic cells," *J. Immunol.* (2003) 171:5140-5147.

Honey, K. et al., "Thymocyte expression of cathepsin L is essential for NKT cell development," *Nat. Immunol.* (2002) 3:1069-1074.

Iida, N. et al., "A sulfated glucosylceramide from rat kidney," *J. Biol. Chem.* (1989) 264(10):5974-5980.

Islam, I. et al., "Synthesis and antiviral activity of (2-((4-(3-((l-methylethyl)amino)-2-pyridyl)-1- piperazinyl)carbony)-1H-1-indo 1-5-yl) (BHAP) acylspingosine HIV reverse transcriptase inhibitors," Biorg. Chem. (1995) 23(4):499-511.

Ismail, N. et al., "Overproduction of TNF-alpha b CD8+ type 1 cells and down-regulation of IFN-γ production by CD4+ Th1 cells contribute to toxic shock-like syndrome in an animal model of fatal monocytotropic ehrlichiosis," *J. Immunol.* (2004) 172:1786-1800.

Kamijuku et al., "Mechanism if NKT cell activation by intranasal coadministration of alpha-galactosylceramdie, which can induce cross-protection against influenza viruses," *Mucosal Immunology* (2008) 1(3):208-218. XP002558333.

Karadimitris, A. et al., "Human CD1d-glycolipid tetramers generated by in vitro oxidative refolding chromatography," *Proc. Natl. Acad. Sci. USA* (2001) 98(6):3294-3298.

Kawano, T. et al., "CD1d-restricted and TCR-mediated activation of Vα14 NKT cells by glycosyceramides," *Science* (1997) 278:1626-1629.

Khan, M. et al., "Syntheses and Antiinflammatory Activity of Some 6-aryl-2,3,4,5-tetrahydro-3-pyridazinones," *Indian J. Chem.* (2000) 39B:614-619.

Kinjo, Y. et al., "Recognition of bacterial glycosphingolipids by natural killer T cells," *Nature* (2005) 434:520-525.

Kitamura, H. et al., "The natural killer T (NKT) cell ligand alpha-galactosylceramide demonstrates its immunopotentiating effect by inducing interleukin (IL)-12 production by dendritic cells and IL-12 receptor expression on NKT cells," *J. Exp. Med.* (1999) 189:1121-1127.

Kopecky-Bromberg et al., "Alpha-C-galactosylceramide as an adjuvant for a live attenuated influenza virus vaccine," *Vaccine, Butterworth Scientific Guildford* (2009) 27 (28): 3766-3774. XP026134053.

Kronenberg, M., "Toward an understanding of NKT cell biology: progress and paradoxes," *Ann. Rev. Immunol* (2005) 23:877-900.

Lee, P.T. et al., "Testing the NKT cell hypothesis on human IDDM pathogenesis," *J. Clin. Invest.* (2002) 110(6):793-800.

Liu, Y. et al., "A modified alpha-galactosyl ceramide for staining and stimulating natural killer T cells," *J. Immun. Meth.* (2006) 312(1-2):34-39.

Matsuda, J.L. et al., "Tracking the response of natural killer T cells to a glycolipid antigen using CD1d tetramers," *J. Exp. Med.* (2000) 192(5):741-753.

Mattner, J. et al., "Exogenous and endogenous glycolipid antigens activate NKT cells during microbial infections," *Nature* (2005) 434:525-529.

Miyamoto, K. et al., "A Synthetic Glycolipid Prevents Autoimmune Encephalomyelitis by Inducing TH2 Bias of Natural Killer T Cells," *Nature* (2001) 413:531-534.

Morita, M. et al., "Structure-Activity Relationship of α-Galactosylceramides Against B16-Bearing Mice," *J. Med. Chem.* (1995) 38:2176-2187.

Nakagawa, R. et al., "Mechanisms of the Antimetastatic Effect in the Liver and of the Hepatocyte Injury Induced by α-Galactosylceramide in Mice," *J. Immun.* (2001) 166:11:6578-6584.

Pal, E. et al., "Costimulation-Dependent Modulation of Experimental Autoimmune Encephalomyelitis by Ligand Stimulation of Vα14 NK T Cells," *J. Immunol.* (2001) 166:662-668.

Park, S.H. et al., "CD1-restricted T-cell responses and microbial infection," *Nature* (2000) 406:788-792.
Park, S.H. et al., "The Mouse CD1d-restricted Repetoire is Dominated by a Few Autoreactive T cell Receptor Families," *J. Exp. Med.* (2001) 8:893-904.
Park, S.-H. et al., "Tissue-specific recognition of mouse CD1 molecules," *J. Immunol.* (1998) 160:3128-3134.
Petrovsky, N. et al., "Vaccine adjuvants: current state and future trends," *Immunol. Cell Biol.* (2004) 82:488-496.
Prigozy, T.I. et al., "Glycolipid antigen processing for presentation by CD1d molecules," *Science* (2001) 291:664-667.
Rock, K.L. et al., "Natural endogenous adjuvants," *Springer Semin. Immunopathol.* (2005) 26:231-24.
Sakai, T. et al., "Effects of α- and β-Galactosylated C2-Ceramides on the Immune System," *J. Med. Chem* (1998) 41:650-652.
Sidobre, S. et al., "CD1d tetramers: a powerful tool for the analysis of glycolipid reactive T cells," *J. Immunol. Methods* (2002) 268:107-121.
Sinay, P. et al., *Bioorganic and Medicinal Chemistry* (1998) 6: 1337-46.
Singh et al., "The natural killer T Cell ligand Alpha-Galactosylceramide protects mice against EAE by an IL-4-and IL-10- dependent mechanism," *FASEB J., Fed. Of Amer. Soc. For Exp. Bio* (2002) 16: A1043.
Singh, P.P. et al., "The Synthesis of 2,3,4,6,7-Penta-O-Methyl-D-glycero-L-manno-Heptose and 2,4,6,7-Tetra-O-Methyl-D-glycero-L-manno-Heptose," *Carbohydrate Res.* (1970) 12:261-266.
Smyth, M.J. et al., "NKT cells—conductors of tumor immunity?" *Curr. Opin. lmmunol.* (2002) 14(2):165-171.
Smyth, M.J. et al., "NKT cells and tumor immunity—a double-edged sword," *Nature Immunology* (2001) 1:459-460.
Stanic A.K. et al., "Defective presentation of the CDId1-restricted natural Val4Ja18 NKT lymphocyte antigen caused by Beta-D-glucosylceramide synthase deficiency," *Proc. Natl. Acad. Sci. USA* (2003) 100:1849-1854.
Supplementary Search Report of the European Patent Office for Application No. 03816701.1 dated Sep. 17, 2007.
Takikawa et al., "Diastereoselective Epoxidation of the Double Bond at C-4 of Sphinogosines to Provide Phytosphingosine Relatives such as α-Galactosylceramide KRN7000," *Tetrahedron* (1998) 54:3141-3150.
The Merck Manual, 16$^{th}$ Edition (1999): pp. 339-342 and 1488-1490.
United States Office Action for U.S. Appl. No. 10/550,165 mailed Oct. 27, 2008.
United States Office Action for U.S. Appl. No. 10/550,165 mailed Jan. 9, 2008.
United States Office Action for U.S. Appl. No. 10/550,165 mailed Jul. 20, 2007.
United States Office Action for U.S. Appl. No. 10/550,165 mailed Apr. 12, 2007.
United States Office Action for U.S. Appl. No. 11/218,906 dated Nov. 10, 2008.
United States Office Action for U.S. Appl. No. 11/771,128 dated Oct. 29, 2008.
United States Office Action for U.S. Appl. No. 12/624,048 mailed Sep. 29, 2010.
United States Notice of Allowance for U.S. Appl. No. 12/296,169 mailed Oct. 26, 2011.
United States Office Action for U.S. Appl. No. 12/296,169 mailed May 11, 2011.
Van Der Vliet, H.J.J. et al., "Effects of α-galactosylceramide (KRN7000), interleukin-12 and interleukin-7 on phenotype and cytokine profile of human Vα24+ Vβ11+T cells," *Immunology* (1999) 98:557-563.
Van Kaer, L., "Alpha-galactosylceramide therapy for autoimmune diseases: prospects and obstacles," *Nat. Rev. Immunol.* (2005) 5:31-42.
Vandommelen, S.L.H. et al., "Activation of natural killer (NK) T cells during murine cytomegalovirus infection enhances the antiviral response mediated by NK cells," *J. Virology* (2003) 77(3):1877-1884.
Vaultier, M. et al., "Reduction d'azides en amines primaires par une methode generale utilisant la reaction de staudinger," *Tetrahedron Letters* (1983) 24:763 (Not in English).
Wang, B. et al., "CD1-Restricted NK T Cells Protect Nonobese Diabetic Mice from Developing Diabetes," *J. Exp. Med.* (2001) 194:313-319.
Wang, F. et al., "Tuning of Binding Selectivity: Metal Control of Organic Guest Binding and Allosteric Perturbation of Fluorescent Metal Sensor," *J. Org. Chem.* (1999) 64:8922-8928.
Weber, G. et al., "Synthesis and Spectral Properties of a Hydrophobic Fluorescent Probe: 6-Propionyl-2-(dimethylamino) naphthalene," *Biochem.* (1979) 18:14:3075-3078.
Winau, F. et al., "Saposin C is required for lipid presentation by human CD1b," *Nat. Immunol.* (2004) 5:169-174.
Wu et al., "Bacterial glycolipids and analogs as antigen for CD1d-restricted NKT cells," *PNAS* (2005) 102(5):1351-1356.
Wu, D.Y. et al., "Cross-presentation of disialoganglioside GD3 to natural killer T cells," *J. Exp. Med.* (2003) 198:173-181.
Xia, C. et al., "Thio-isoglobotrihexosylceramide, an Agonist for activating invariant natural killer T cells," *Org. Lett.* (2006) 8(24):5493-5496.
Yu, K.O.A. et al., "Modulation of CD1d-restricted NKT cell responses by using N-acyl variants of alpha-galactosylceramides," *Proc. Natl. Acad. Sci. USA* (2005) 102(9):3383-3388.
Zajonc, D.M. et al., "Structural basis for CD1d presentation of a sulfatide derived from myelin and its implications for autoimmunity," *J. Exp. Med.* (2005) 202(11):1517-1526.
Zajonc, D.M. et al., "Structure and function of a potent agonist for the semi-invariant natural killer T cell receptor," *Nat. Immunol.* (2005) 6:810-818.
Zhou et al., "Synthesis and NKT cell stimulating properties of fluorophore-and biotin-appended 6"-amino-6"-deoxy-galactosylceramides," *Org. Lett.* (2002) 4(8):1267-1270. XP003008968.
Zhou, D. et al., "Editing of CD1d-bound lipid antigens by endosomal lipid transfer proteins," *Science* (2004) 303:523-527.
Zhou, D. et al.,"Lysosomal glycosphingolipid recognition by NKT cells," *Science* (2004) 306:1786-1789.
Zhou, D., "The immunological function of iGb3," *Curr. Prot. Pept. Sci.* (2006) 7:325-333.
International Search Report for Application No. PCT/EP2009/062894.
Written Opinion for Application No. PCT/EP2009/062894.
International Search Report for Application No. PCT/US2005/031407.
Written Opinion for Application No. PCT/US2005/031407.
International Search Report for International Application No. PCT/US2007/072451.
Written Opinion for International Application No. PCT/US2007/072451.
International Search Report for International Application No. PCT/US06/002781.
Written Opinion for International Application No. PCT/US06/002781.
International Search Report for International Application No. PCT/US07/66250.
Written Opinion for International Application No. PCT/US07/66250.
International Search Report for International Application No. PCT/US03/08530.
Written Opinion for International Application No. PCT/US03/08530.

* cited by examiner

COMPOSITIONS FOR AND METHODS OF ENHANCING THE IMMUNE RESPONSE TO ANTIGENS

CROSS-REFERENCE TO RELATED APPLICATIONS

This application is a National Stage Application of PCT/IB2008/003945, filed 5 Dec. 2008, which claims benefit of U.S. Ser. No. 60/992,460, filed 5 Dec. 2007 and which applications are incorporated herein by reference. To the extent appropriate, a claim of priority is made to each of the above disclosed applications.

INTRODUCTION

The fundamental purpose of a vaccine is to provide lasting immunity against a pathological condition. Ideally, vaccines provide functionally active antibodies, elicit cell-mediated immunity, and activate T- and B-lymphocytes with highly specific reactivity as well as "memory" to provide protection against further encounters with antigen.

Adjuvants are vaccine additives which nonspecifically augment the immune response. The mechanisms by which adjuvants enhance the immune system vary widely. Adjuvants may be classified as "immunomodulatory" or "antigen delivery" systems. Immunomodulatory adjuvants prime the immune system by regulating the action of immune cells through alteration of lymphokine production. Antigen delivery systems, on the other hand, function to deliver the antigen to the appropriate immune cells. In addition, adjuvants may enhance the speed or duration of an immune response, modulate antibody avidity, specificity, isotype or subclass distribution, stimulate cell mediated immunity, promote mucosal immunity, or enhance the immune responses in immunologically immature or senescent individuals. Adjuvants can affect the innate, humoral or cell-mediated immune response, or a combination thereof.

SUMMARY OF INVENTION

The inventors have discovered that a synthetic glycolipid of a particular class, when used in combination with a vaccine preparation is capable of activating both humoral and cellular immune responses when administered to a subject. Accordingly, the invention provides compositions comprising compounds of formula I, wherein formula I is shown below:

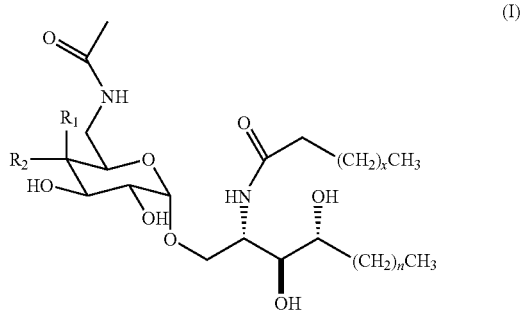

(I)

where $R_1$ and $R_2$ are independently selected from —H or —OH, x is an integer from 18 to 26 and n is an integer from 10 to 15. Compositions including the compound of formula I and an antigen are also provided.

In another aspect, the invention provides methods of enhancing the immune response in a subject to an antigen by administering a composition including the compound of formula I and an antigen. The enhanced immune response may be a humoral immune response, a CD4+ T cell response, a CD8+ cytotoxic T cell response or activation of antigen presenting cells (APCs). The immune response of the subject is enhanced relative to an appropriate control.

In a further aspect, the compositions of the invention are administered intramuscularly.

DETAILED DESCRIPTION OF SEVERAL EMBODIMENTS

Figure 1:
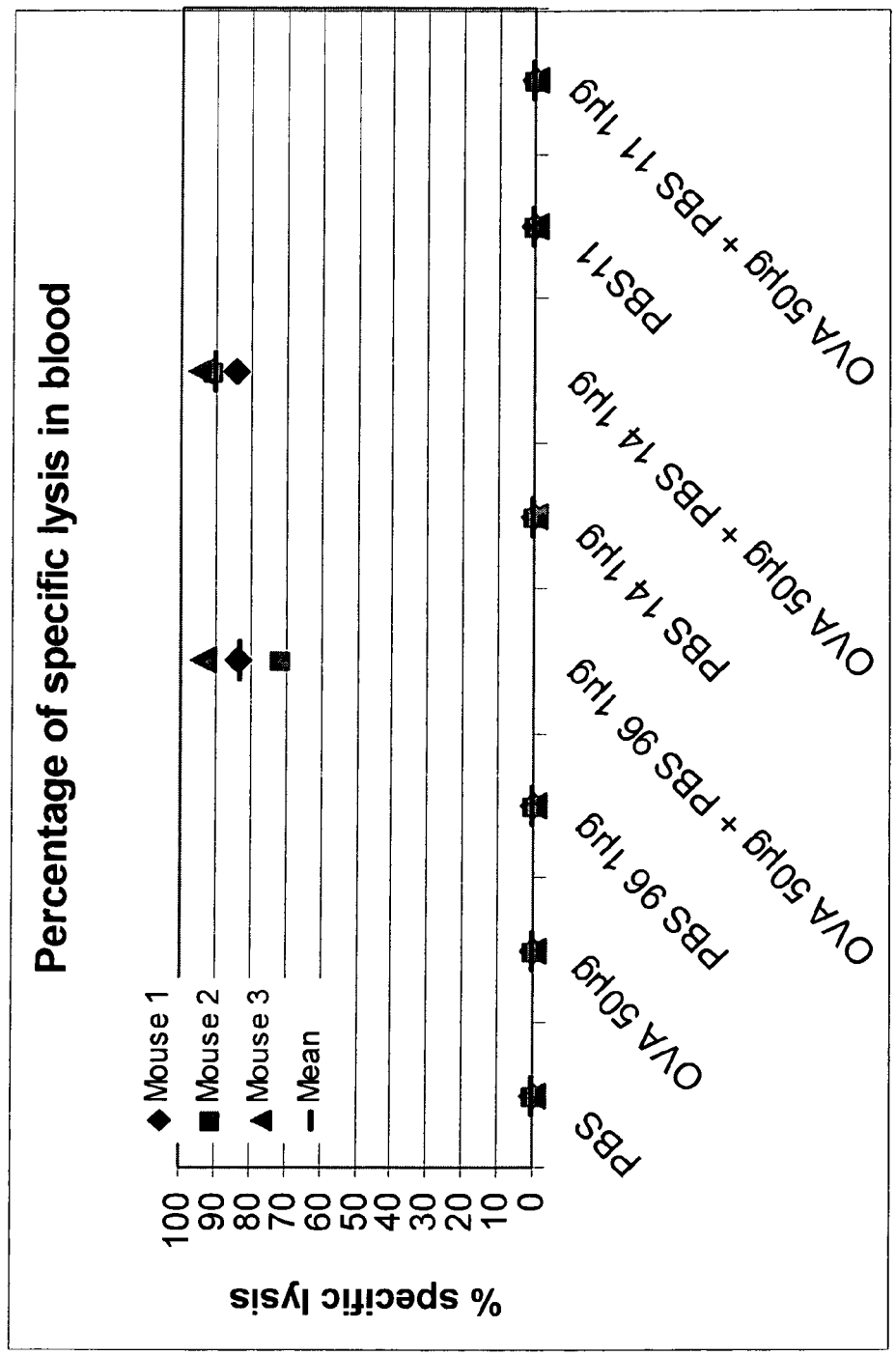
FIG. 1 is a graph depicting the percentage of specific lysis of Ova-specific target cells in the blood of mice injected intravenously (IV) with PBS-96, PBS-14 or PBS-11, with or without Ova.

Adjuvants enhance the immunogenicity of antigens in vaccine preparations in a variety of ways. An effective adjuvant also would be useful for combination with a wide variety of antigens to enhance the immune response elicited by administration of the antigen. For example, in the case of toxins, a good humoral immune response is required. In the case of intracellular bacteria, a cell-mediated response, mediated mainly by cytotoxic T cells and Th1 cells, is important. In the case of viral infections, both humoral and cellular responses are fundamental to control the infection. The ability of an adjuvant to enhance not only the humoral but also the cell-mediated immune response increases the likelihood of developing long-lasting immunity.

Lipid species have been investigated for adjuvant properties. A number of natural and synthetic lipid molecules are processed by antigen-presenting cells and presented by CD1 molecules to NKT cells. The prototypical compound used to study NKT cell activation in vitro and in vivo is KRN7000, an α-galactosyceramide ("αGalCer") derived from marine sponge *Agelas mauritianus*. Additional compounds recently identified include isoglobotrihexosylceramide ("iGB3") which is an endogenous glycolipid and modified 6"amino 6" deoxygalactosyceramides, as described in PCT Application PCT/US07/66250, the disclosure of which is incorporated herein by reference. These compounds activate NKT cells and upregulate cytokine responses in vitro. However, in the context of in vivo vaccinations, little is known regarding the effectiveness of lipid adjuvanticity for these compounds.

The inventors have found that glycosphingolipids of formula I containing an amino group and a saturated fatty acid chain, unexpectedly have the ability to stimulate both a cell-mediated and humoral immune response in vivo. In addition, compounds of formula I are able to stimulate an immune response against a weak nominal antigen to produce antibodies and simultaneously provide for cell-mediated lysis of cells expressing specific surface antigens. Two compounds of formula I, designated PBS-96 and PBS-14, were shown to stimulate both cell-mediated and humoral immune responses in vivo. These compounds also stimulated an immune response against a weak nominal antigen to produce antibodies and elicit a cell-mediated response. In addition, these compounds were found to stimulate a more robust response when injected intramuscularly or at lower doses as compared to other glycoshingolipids such as PBS-57 and αGalCer.

In one embodiment, the invention provides a composition comprising a compound of formula I, where formula I is:

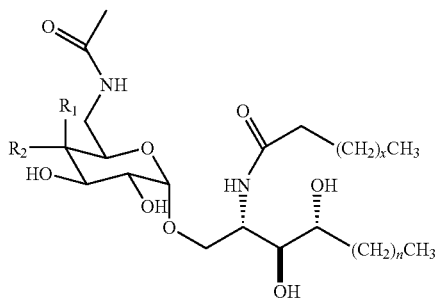

(I)

where $R_1$ and $R_2$ are independently selected from —H or —OH, x is an integer from 18 to 26 and n is an integer from 10 to 15. Compounds of formula I suitably have an amide group at the C6 position of the galactose or glucose molecule and a saturated acyl chain at the ceramide portion of the compound. The composition may further include a physiological acceptable carrier. A "physiologically acceptable" carrier is any carrier that is suitable for in vivo administration (e.g., oral, transdermal or parenteral administration) or in vitro use, i.e., cell culture. Suitable physiologically acceptable carriers for in vivo administration include water, buffered solutions and glucose solutions, among others. Additional components of the compositions can include excipients such as stabilizers, preservatives, diluents, emulsifiers or lubricants in addition to the physiologically acceptable carrier. Suitable excipients include, but are not limited to, Tween 20, DMSO, sucrose, L-histadine, polysorbate 20 and serum. Suitably the compound of formula I is formulated in a liposome. Suitably the liposome is a type SUV comprised of phosphatidyl choline (PC)/phosphatidyl glycerol (PG)/Cholesterol in a ratio of 8 μmoles/2 μmoles/5 μmoles/1 mg. Those skilled in the art will appreciate the compound of formula I may be formulated in a variety of ways for administration to a subject.

In another embodiment, the invention provides methods of enhancing an immune response to an antigen in a subject by administering a composition containing the compound of formula I and the antigen. As used herein, a "subject" is a mammal, e.g., a mouse, or more suitably a human. "Enhancing the immune response" refers to the ability of the compound to enhance the humoral and/or cell mediated immune response of a subject to the antigen in relation to a suitable control. Increased activation of antigen presenting cells is also included as an enhanced immune response of the subject. For purposes of determining whether the immune response is enhanced relative to a control, a quantitative comparison of the signal in a sample from a subject vaccinated with antigen and the compound can be compared to the signal in a sample from a subject vaccinated with antigen alone. The immune response to the antigen may be measured in a variety of ways which will be apparent to those skilled in the art. In the Examples, the immune response is measured by way of a cytotoxic specific cell lysis assay, a pentamer binding assay, or an ELISA assay, the performance of which is routine to those skilled in the art.

In particular embodiments, the immune response is enhanced at least 25%, at least 30%, at least 50%, at least 60%, at least 65%, at least 70%, at least 75%, at least 80%, at least 85%, at least 90%, at least 95%, at least 100%, at least 150%, at least 200%, at least 400%, at least 500%, at least 750% or at least 1000%, relative to a suitable control. A suitable control is a subject who has been administered an antigen but not a composition of the invention. Percent enhancement may be calculated using the following formula:

[(value representing subject's immune response after treatment with composition containing the compound of formula I)−(value representing immune response of control)/(value representing subject's immune response after treatment with composition containing the compound of formula I)]× 100.

As used herein, the terms "administration", "co-administration" and "co-administering" refer to administration of the adjuvant and the antigen concurrently, i.e., simultaneously in time, or sequentially, i.e., administration of the adjuvant followed by administration of the antigen, or administration of the antigen followed by administration of the adjuvant. After administration of the adjuvant or antigen, the other component can be administered substantially immediately thereafter or after an effective time period thereafter; the effective time period is the amount of time given for realization of maximum benefit from the administration of the components. Alternatively, the adjuvant and antigen may be co-formulated.

Figure 13:
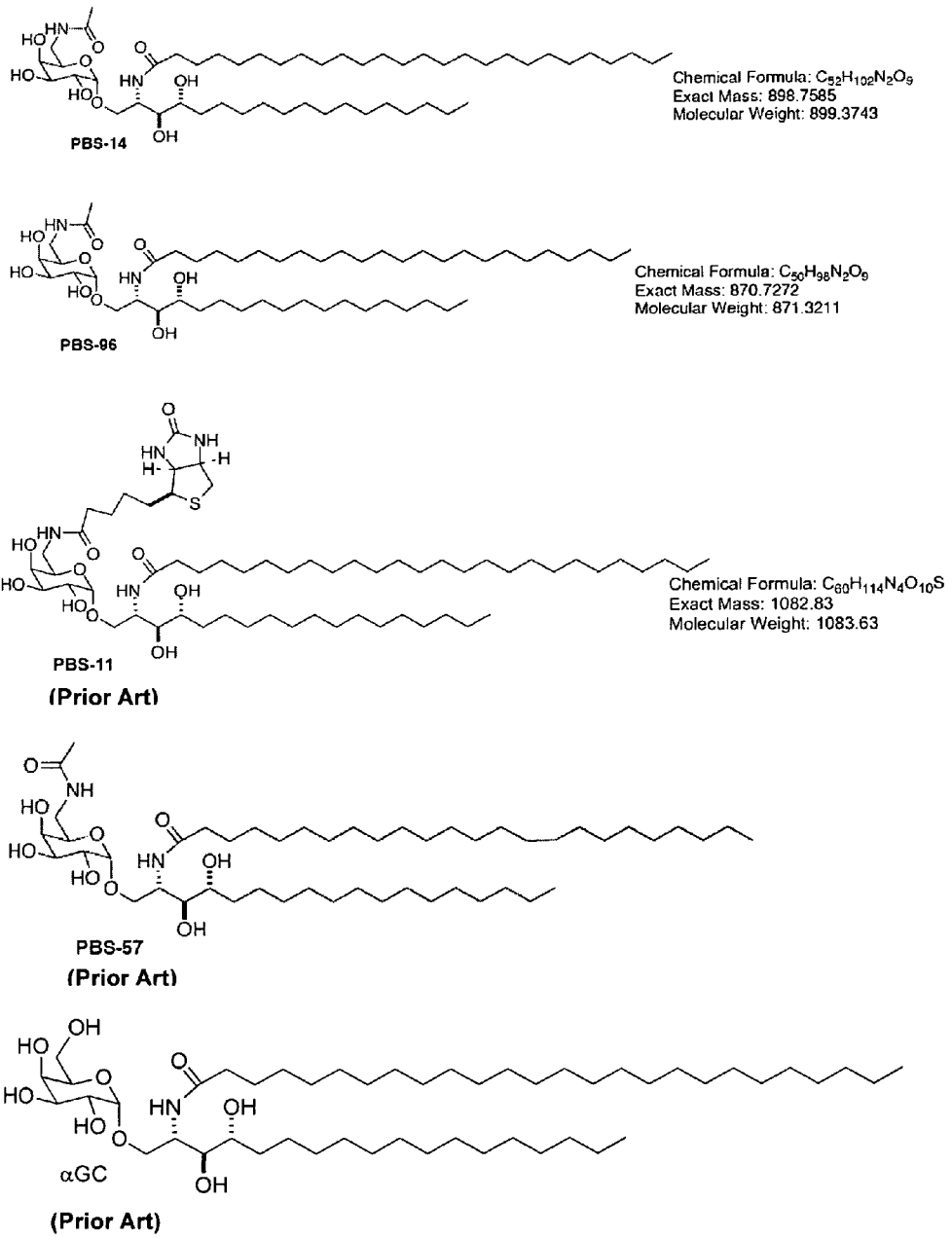
FIG. 13 depicts structural formulae for PBS-14, PBS-96, PBS-11, PBS-57 and αGalCer.

The antigen may be a polypeptide, polynucleotide, or carbohydrate moiety, or combinations thereof, for example, a glycoprotein. The antigen is suitably derived from an infectious agent (e.g., a pathogenic microorganism), a tumor, an endogenous molecule (e.g., a "self" molecule), or, for purposes of study, a nominal antigen, such as ovalbumin (referred to herein as "OVA"). Suitably the antigen is encompassed within a vaccine. Vaccine compositions are suitably formulated to include the compound of formula I. "Vaccine" refers to a composition which, when administered to a subject, induces cellular or humoral immune responses. Pharmaceutical compositions used in conjunction with the invention suitably include the compound of formula I and a vaccine. In some embodiments, the pharmaceutical compositions used in conjunction with the invention suitably include PBS-96 and an antigen or PBS-14 and an antigen. The structures of PBS-96 and PBS-14 are shown in FIG. 13. PBS-96 and PBS-14 activate NKT cells in vitro and in vivo. Both PBS-96 and PBS-14 contain an amide group at the C6 position of the galactose and a saturated acyl chain at the ceramide portion of the compound. PBS-96 and PBS-14 enhance the CD8+ T cell response to an antigen and PBS-96 and PBS-14 induce the release of IFN-γ in vivo. In addition, PBS-96 and PBS-14 are unexpectedly superior to other glycosphingolipids when used at lower concentrations and also when injected intramuscularly.

Compositions including compounds of formula I may be formulated using a variety of preparative methods and inactive ingredients known to those of skill in the art. (Remington's Pharmaceutical Sciences, Mack Publishing Co., (2000), which is incorporated herein by reference.) Compositions of the invention may also contain a suitable antigen delivery system to target the antigen to immune cells. Antigen delivery systems are known in the art, and include, but are not limited to, MVA (Modified virus ankara), adenovirus, lentivirus, translocated subunit of pertussis or shiga toxin, or antigen encapuslated liposomes. Effective dosages of the compound of formula I in a vaccine composition may be determined by those of skill in the art, but typically range from about 1 nanogram to about 10,000 micrograms per kilogram of body weight, although they are typically about 1,000 micrograms or less per kilogram of body weight. In some embodiments, the effective dosage ranges from about 10 nanograms to about 1,000 micrograms per kilogram of body weight. In another embodiment, the effective dosage ranges from about 100 nanograms to about 500 micrograms per kilogram of body weight. In another embodiment, the effective dosage ranges from about 1 microgram to about 250 micrograms per kilogram of body weight. For purposes of study, a suitable dosage for a mouse is from 1 ng to 1 µg compound of formula I per 100 µl dose depending on route of administration. For example, dosage of about 100 ng is suitable for intravenous injection in a mouse and dosage of as little as 10 ng was shown to be effective for intramuscular injection. The composition comprising the compound of formula I can be administered in a single dose, or split into multiple doses over a period of weeks or months.

One or more antigens may be included in the compositions or may be formulated independently. As used herein, an "antigen" refers to a molecule that stimulates an immune response in a subject to which it has been administered. It will be appreciated that the dosage of antigen will depend on the specific antigen, and on the age and immune status of the subject, as well as other relevant factors that may be determined by those skilled in the art.

Whole microorganisms or portions thereof (e.g., membrane ghosts; crude membrane preparations, lysates and other preparations of microorganisms) may be utilized as antigens. Suitably, antigens are derived from attenuated or killed infectious agents. Suitable infectious agents from which an antigen may be derived include, but are not limited to, pathogens and microorganisms such as bacteria, parasites and viruses. In some contexts, suitable antigens are obtained or derived from a viral pathogen that is associated with human disease including, but not limited to, HIV/AIDS (Retroviridae, e.g., gp120 molecules for HIV-1 and HIV-2 isolates, HTLV-I, HTLV-11), influenza viruses (Orthomyxoviridae, e.g., types A, B and C), herpes (e.g., herpes simplex viruses, HSV-1 and HSV-2 glycoproteins gB, gD and gH), rotavirus infections (Reoviridae), respiratory infections (parainfluenza and respiratory syncytial viruses), Poliomyelitis (Picornaviridae, e.g., polioviruses, rhinoviruses), measles and mumps (Paramyxoviridae), Rubella (Togaviridae, e.g., rubella virus), hepatitis (e.g., hepatitis viruses types A, B, C, D, E and/or G), cytomegalovirus (e.g., gB and gH), gastroenteritis (Caliciviridae), Yellow and West Nile fever (Flaviviridae), Rabies (Rhabdoviridae), Korean hemorrhagic fever (Bunyaviridae), Venezuelan fever (Arenaviridae), warts (Papillomavirus), simian immunodeficiency virus, encephalitis virus, varicella zoster virus, Epstein-Barr virus, and other virus families, including Coronaviridae, Birnaviridae and Filoviridae.

Suitable bacterial and parasitic antigens can also be obtained or derived from known disease-causing agents and may be used in compositions to vaccinate against diseases including, but not limited to, diphtheria, pertussis, tetanus, tuberculosis, bacterial or fungal pneumonia, otitis media, gonorrhea, cholera, typhoid, meningitis, mononucleosis, plague, shigellosis or salmonellosis, Legionnaires' disease, Lyme disease, leprosy, malaria, hookworm, onchocerciasis, schistosomiasis, trypanosomiasis, leishmaniasis, giardiases, amoebiasis, filariasis, Borrelia, and trichinosis. Still further antigens can be obtained or derived from unconventional pathogens such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

Additional specific pathogens from which antigens can be derived include *M. tuberculosis, Chlamydia, N. gonorrhoeae, Shigella, Salmonella, Vibrio cholerae, Treponema pallidum, Pseudomonas, Bordetella pertussis, Brucella, Francisella tularensis, Helicobacter pylori, Leptospira interrogans, Legionella pneumophila, Yersinia pestis, Streptococcus* (types A and B), pneumococcus, meningococcus, *Haemophilus influenza* (type b), *Toxoplasma gondii, Moraxella catarrhalis*, donovanosis, and actinomycosis; fungal pathogens include candidiasis and aspergillosis; parasitic pathogens include *Taenia*, flukes, roundworms, amebiasis, giardiasis, *Cryptosporidium, Schistosoma, Pneumocystis carinii*, trichomoniasis and trichinosis. The present invention can also be used to provide a suitable immune response against numerous veterinary diseases, such as foot-and-mouth diseases, coronavirus, *Pasteurella multocida, Helicobacter, Strongylus vulgaris, Actinobacillus pleuropneumonia*, Bovine Viral Diarrhea Virus (BVDV), *Klebsiella pneumoniae, E. coli*, and *Bordetella pertussis, parapertussis* and *brochiseptica*.

In other embodiments, antigens for inclusion in compositions that may be used in conjunction with the present invention are tumor-derived antigens or autologous or allogeneic whole tumor cells. Suitably, the tumor antigen is a tumor specific antigen (TSA) or a tumor associated antigen (TAA). Several tumor antigens and their expression patterns are known in the art and can be selected based on the tumor type to be treated. Non-limiting examples of tumor antigens include cdk4 (melanoma), β-catenin (melanoma), caspase-8 (squamous cell carcinoma), MAGE-1 and MAGE-3 (melanoma, breast, glioma), tyrosinase (melanoma), surface Ig idiotype (e.g., BCR) (lymphoma), Her-2/neu (breast, ovarian), MUC-1 (breast, pancreatic) and HPV E6 and E7 (cervical carcinoma). Additional suitable tumor antigens include prostate specific antigen (PSA), sialyl Tn (STn), heat shock proteins and associated tumor peptides (e.g., gp96), ganglioside molecules (e.g., GM2, GD2, and GD3), Carcinoembryonic antigen (CEA) and MART-1.

As appreciated by skilled artisans, pharmaceutical compositions are suitably formulated to be compatible with the intended route of administration. Examples of suitable routes of administration include parenteral, e.g., intravenous, intradermal, subcutaneous, intramuscular, oral (e.g., inhalation), enteral, transdermal (topical), transmucosal, and rectal administration. As shown in the Examples, the compounds of formula I were found to provide an unexpectedly robust enhancement of the immune response after intramuscular administration.

Another embodiment of the invention is a method of stimulating a humoral immune response to an antigen. The method includes co-administering a compound of formula I and an antigen to a subject, as described above. As used herein, a "humoral immune response" refers to the production of antibodies by B cells, and the accessory process that accompanies it, including, but not limited to, e.g., Th2 activation and cytokine production, germinal center formation and isotype switching, affinity maturation production and memory cell generation. For purposes of determining whether a humoral immune response is activated, a quantitative comparison of the signal in a sample from a subject administered antigen and a compound of formula I can be compared to a sample from a subject administered antigen alone. The humoral immune response may be evaluated by measuring the effector functions of antibodies, including pathogen or toxin neutralization, classical complement activation, and opsonin promotion of phagocytosis and pathogen elimination. The antibodies produced in response to co-administering the compound of formula I and an antigen may be of any type, e.g., IgM, IgA, or IgG (such as IgG1 or IgG2). The humoral immune response may be assayed by any quantitative method known in the art, e.g., ELISA, single radial immunodiffusion assay (SRID), enzyme immunoassay (EIA), or hemagglutination inhibition assay (HAI).

A further embodiment of the invention is a method of activating CD4+ T lymphocytes in a subject. As understood in the art, CD4+ T cells, or "T helper cells," are cells that recognize antigens presented by class II major histocompatability marker (MHC) on the surface of antigen presenting cells, and secrete lymphokines to stimulate both cell-mediated and antibody-mediated branches of the immune system. CD4+ T cell activation promotes lymphokine secretion, immunoglobulin isotype switching, affinity maturation of the antibody response, macrophage activation and enhanced activity of natural killer (NK) and cytotoxic T cells (CTL). Lymphokines are proteins secreted by lymphocytes that affect their own activity and/or the activity of other cells. Lymphokines include, but are not limited to, interleukins and cytokines, e.g., IL-2, IL-4, IL-5, IL-6, IL-10, IL-12, or IFNγ. For purposes of determining whether a CD4+ T lymphocytes are activated, a quantitative comparison of the signal in a sample from a subject vaccinated with antigen and a compound of formula I can be compared to a sample from a subject vaccinated with antigen alone. Methods to assay activation CD4+ T cells are known in the art.

Another embodiment of the invention is a method of activating CD8+ T lymphocytes in a subject. CD8+ T lymphocytes recognize antigens presented by Class I MHC molecules (present on all nucleated cells). Engagement of the MHC class-I peptide complex results in delivery of lytic granules to the target cell causing lysis of the target cell. Methods used to assay the activation of CD8+ T cells are known in the art, and include, but are not limited to, ELISPOT, ELISA, FACS analysis for tetramer/pentamer binding, and cytotoxic assays. Alternatively, a mouse model may be used to monitor the activation of CD8+ T cells using a fluorescent assay to measure cell-mediated cytotoxicity, as described in Hermans et al, 2004, *Journal of Immunologic Methods*, 285:25-40, incorporated by reference in its entirety. In this assay, mice are immunized on day 0 with the vaccine with or without the test compound. Syngeneic target cells are created by isolating splenocytes from a second set of mice and labeling the cells with two separate cell-labeling fluorescent dyes or high and low concentrations of a single fluorescent dye, e.g., CFSE or CMTMR. One set of target cells is loaded with antigen-specific peptides while a second set of target cells is loaded with an irrelevant peptide. The two target cell populations are mixed in equal amounts and injected into immunized mice. 24 hours later, mice are sacrificed, and splenocytes and blood samples are obtained. The levels of each set of target cells are analyzed by flow cytometry. Activation of CD8+ lymphocytes is determined by comparing the number of target cells in a sample vaccinated with antigen and test compound to the number of target cells in a sample from a subject vaccinated with antigen alone.

Other aspects of the invention will become apparent by consideration of the following non-limiting examples and accompanying figures.

EXAMPLES

Example 1

Testing for Enhancement of the CD8+ T Cell Response by PBS-96, PBS-14 and PBS-11 Injected Intravenously in a Mouse Model A mouse model was used to test in vivo specific cytotoxic T cell response (CD8+) elicited by test adjuvant compounds in combination with antigen when administered intravenously. Eight groups of 3 mice were immunized on day 0 with antigen (Ovalbumin, Ova, grade VII, Sigma, St. Louis, Mo.) with or without adjuvant, adjuvant alone, or carrier alone (control) in a total of 100 μl PBS intravenously (lateral tail vein). Test adjuvant compounds were 1 μg PBS-96, 1 μg PBS-14, 1 μg PBS-11 with or without 50 μg Ovalbumin (OVA) antigen.

Syngeneic target cells were prepared by isolating splenocytes from a second set of C57/B1/6J CD45.2 female mice and labeling the cells with either low concentration (0.6 over 8 min at 37° C.) or high concentration (6 μM over 8 minutes at 37° C.) of CFSE (fluorescent dye). The population labeled with high concentration CFSE was pre-loaded with 5 μM SIINFEKL peptide (Ova-specific peptide, NeoMPS, Inc, San Diego, Calif.) over 60 minutes at 37° C. The population labeled with low concentration CFSE was pre-loaded with 5 μl LCMV gp33-41 peptide (non-Ova peptide, NeoMPS, Inc, San Diego, Calif.) over 60 minutes at 37° C. Target cells were mixed with a final ratio of 47/53 of low concentration CFSE loaded cells to high concentration CFSE loaded cells ($2 \times 10^7$ cells total per 100 μl) and injected intravenously into each of the immunized mice on day 10. Mice were sacrificed at day 11, and spleen cells and blood samples from the orbital sinus were collected. The mean percentage survival of the peptide-pulsed target cells (CFSE labeled high concentration) were calculated relative to the control population by flow cytometric analysis. Cytotoxic activity was expressed as percent specific lysis (100 minus the mean percent survival of peptide-pulsed targets). FIG. 1 depicts the percentage of specific lysis of target cells in the blood of immunized mice. Only administration of the combinations of Ova and PBS-96 or PBS-14 resulted in cytotoxic lysis of Ova-specific target cells. In contrast, administration of PBS-11 did not result in specific lysis of cells.

Example 2

Comparison of Enhancement of the CD8+ T Cell Response by PBS-96, PBS-14, PBS-11, PBS-57 and αGalCer when Injected Intravenously and Intramuscularly in a Mouse Model To determine the ability of the test adjuvant compounds to induce an in vivo specific cytotoxic T cell response (CD8+) when administered in combination with antigen, test adjuvant compounds were further assayed using the method described in Example 1. Eighteen groups of mice where immunized on day 0 either intravenously (IV) (groups 1-9 of 3 mice per group) or intramuscularly (groups 10-18 of 6 mice per group) as follows:
  Group 1: 400 µg of Ova into 100 µl of PBS by IV;
  Group 2: 1 µg of αGalCer into 100 µl of PBS by IV;
  Group 3: 1 µg of PBS-57 into 100 µl of PBS by IV;
  Group 4: 1 µg of PBS-14 into 100 µl of PBS by IV;
  Group 5: 1 µg of PBS-96 into 100 µl of PBS by IV;
  Group 6: 400 µg of Ova+1 µg of αGalCer into 100 µl of PBS by IV;
  Group 7: 400 µg of Ova+1 µg of PBS-57 into 100 µl of PBS by IV;
  Group 8: 400 µg of Ova+1 µg of PBS-14 into 100 µl of PBS by IV;
  Group 9: 400 µg of Ova+1 µg of PBS-96 into 100 µl of PBS by IV;
  Group 10: 400 µg of Ova into 50 µl of PBS by IM;
  Group 11: 1 µg of αGalCer into 50 µl of PBS by IM;
  Group 12: 1 µg of PBS-57 into 50 µl of PBS by IM;
  Group 13: 1 µg of PBS-14 into 50 µl of PBS by IM;
  Group 14: 1 µg of PBS-96 into 50 µl of PBS by IM;
  Group 15: 400 µg of Ova+1 µg of αGalCer into 50 µl of PBS by IM;
  Group 16: 400 µg of Ova+1 µg of PBS-57 into 50 µl of PBS by IM;
  Group 17: 400 µg of Ova+1 µg of PBS-14 into 50 µl of PBS by IM;
  Group 18: 400 µg of Ova+1 µg of PBS-96 into 50 µl of PBS by IM.

Target cells were mixed with a final ratio of 50/50 of low concentration CFSE loaded cells to high concentration CFSE loaded cells ($1\times10^7$ cells each concentration, $2\times10^7$ cells total per 100 µl) and injected intravenously into each of the immunized mice on day 10. On day 11, mice were sacrificed and blood samples were collected from the orbital sinus. Cell lysis of the OVA-specific target cells was monitored by flow cytometry of the peripheral blood cells. Specific cell lysis was determined as described above.

Figure 2:
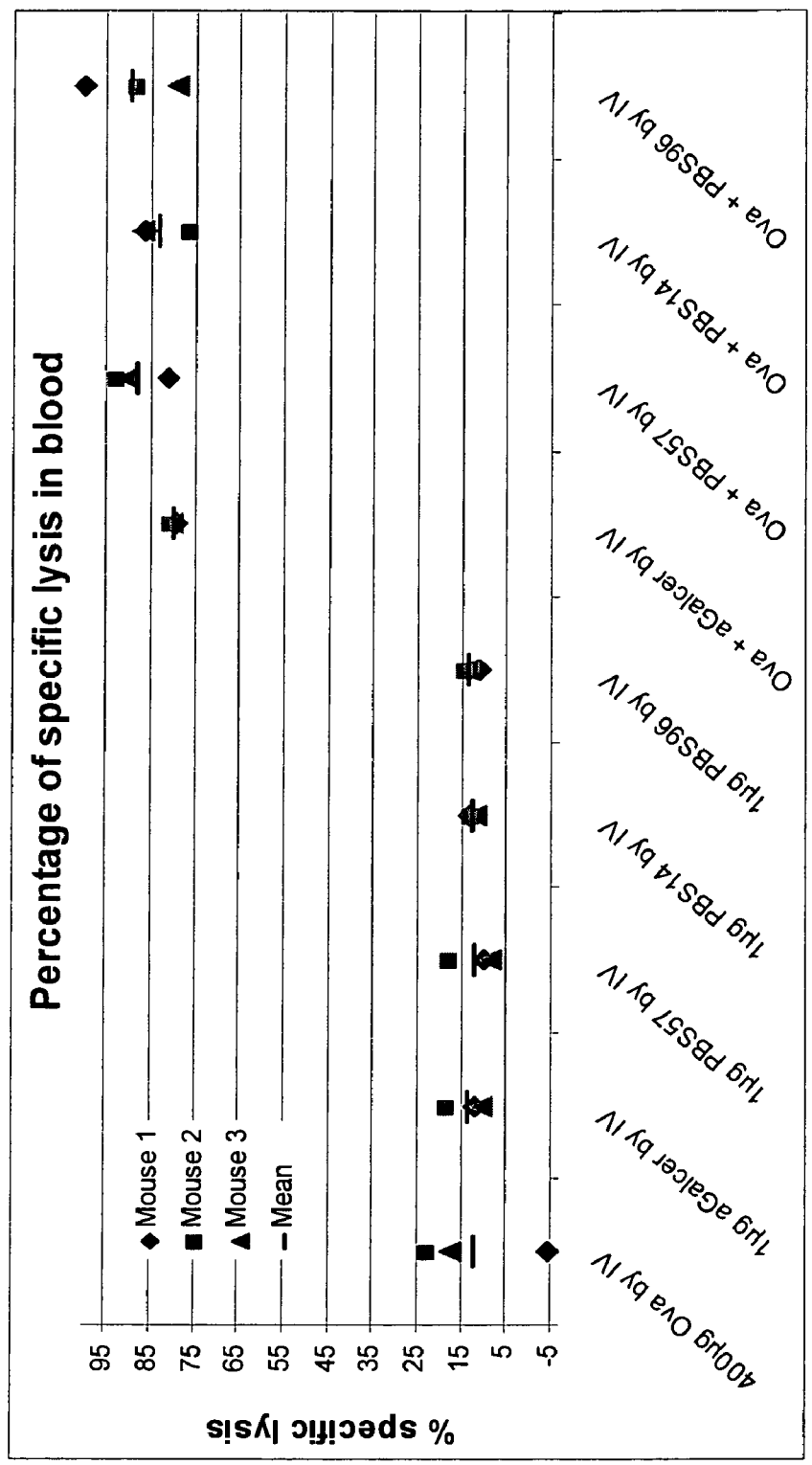
FIG. 2 is a graph depicting the percentage of specific lysis of Ova-specific target cells in the blood of mice injected IV with αGalCer, PBS-57, PBS-96 or PBS-14, with or without Ova.

FIG. 2 shows the results for mice injected intravenously. The average Ova-specific cytotoxic response in mice treated with Ova alone was 11.8±14.4%, with Ova and αGalCer was 79.9±0.8%, in mice treated with Ova and PBS-57 was 88.1±6.2%, in mice treated with Ova and PBS-14 was 83.3±6.1%, and in mice treated with Ova and PBS96 was 89.2±10.3%. Results showed PBS-14 and PBS-96 were as effective as PBS-57 in inducing in vivo OVA-specific cytotoxic responses.

Figure 3:
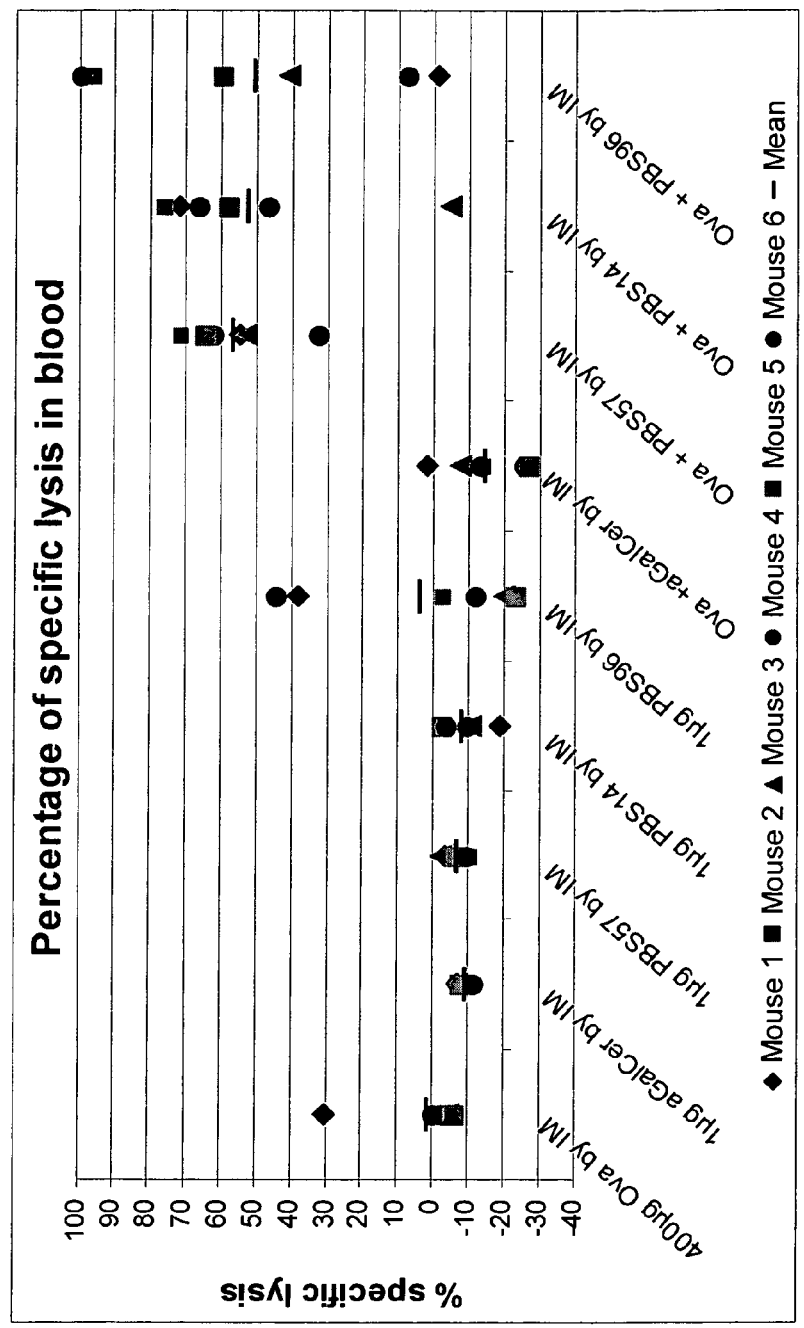
FIG. 3 is a graph depicting the specific lysis of Ova-specific target cells in the blood of mice injected intramuscularly (IM) with αGalCer, PBS-57, PBS-96 or PBS-14, with or without Ova.

FIG. 3 shows the results for mice injected intramuscularly. The average OVA-specific cytotoxic response in mice treated with Ova alone was 1.60±14.33%, in mice treated with OVA and αGalCer was −5.85±11.01%, in mice treated with Ova and PBS-57 was 56.11±13.34%, in mice treated with Ova and PBS-14 was 52.07±29.56%, and in mice treated with OVA and PBS-96 was 50.29±42.6%. These results demonstrate that PBS-96 and PBS-14 both elicit an immune response as effectively as PBS-57 both intravenously and intramuscularly and that PBS-14, PBS-96 and PBS-57 are more effective than αGalCer after intramuscular injection.

Example 3

In Vivo Stimulation of IFNγ by Test Adjuvant Compounds

To test the ability of the adjuvant test compounds to stimulate in vivo cytokine release, C57BL/6 mice were administered the compounds at different concentrations intravenously and the production of IFNγ in sera was measured 24 hours later by ELISA. Groups of 3 mice were inoculated intravenously (tail vein) on day 0 as follows:
  Group 1: 100 µl of PBS alone
  Group 2: 1 µg of αGalCer in 100 µl of PBS
  Group 3: 100 ng of αGalCer in 100 µl of PBS
  Group 4: 1 ng of αGalCer in 100 ml of PBS
  Group 5: 0.1 ng of αGalCer in 100 µl of PBS
  Group 6: 100 ng of αGalCer and 400 µg of Ova in 100 µl of PBS
  Group 7: 1 µg of PBS-57 in 100 µl of PBS
  Group 8: 100 ng of PBS-57 in 100 µl of PBS
  Group 9: 1 ng of PBS-57 in 100 µl of PBS
  Group 10: 0.1 ng of PBS-57 in 100 µl of PBS
  Group 11: 100 ng of PBS-57 and 400 µg of Ova into 100 µl of PBS
  Group 12: 1 µg of PBS-14 in 100 µl of PBS
  Group 13: 100 ng of PBS-14 in 100 µl of PBS
  Group 14: 1 ng of PBS-14 in 100 µl of PBS
  Group 15: 0.1 ng of PBS-14 in 100 µl of PBS
  Group 16: 100 ng of PBS-14 and 400 µg of Ova in 100 µl of PBS
  Group 17: 1 µg of PBS-96 in 100 µl of PBS
  Group 18: 100 ng of PBS-96 in 100 µl of PBS
  Group 19: 1 ng of PBS-96 in 100 µl of PBS
  Group 20: 0.1 ng of PBS-96 in 100 µl of PBS
  Group 21: 100 ng of PBS-96 and 400 µg of Ova in 100 µl of PBS.

24 hours after inoculation, blood samples were collected from the mice and IFNγ levels were detected by ELISA kit. Two ELISA kits were used, Quantikine mouse IFNγ (RD systems) was used to test all samples and ELISA mIFNγ (Diaclone) was used to test group 1, 2, 3, 6, 7, 8, 11, 12, 13, 16, 17, 18 and 21. All sera were diluted before use in ELISA as follows:

| | | |
|---|---|---|
| Group 1: 1/1 | Group 2: 1/50 | Group 3: 1/50 |
| Group 4: 1/20 | Group 5: 1/10 | Group 6: 1/50 |
| Group 7: 1/50 | Group 8: 1/50 | Group 9: 1/20 |
| Group 10: 1/10 | Group 11: 1/50 | Group 12: 1/50 |
| Group 13: 1/50 | Group 814: 1/20 | Group 15: 1/10 |
| Group 16: 1/50 | Group 17: 1/50 | Group 18: 1/50 |
| Group 19: 1/20 | Group 20: 1/10 | Group 21: 1/50 |

Figure 4A:
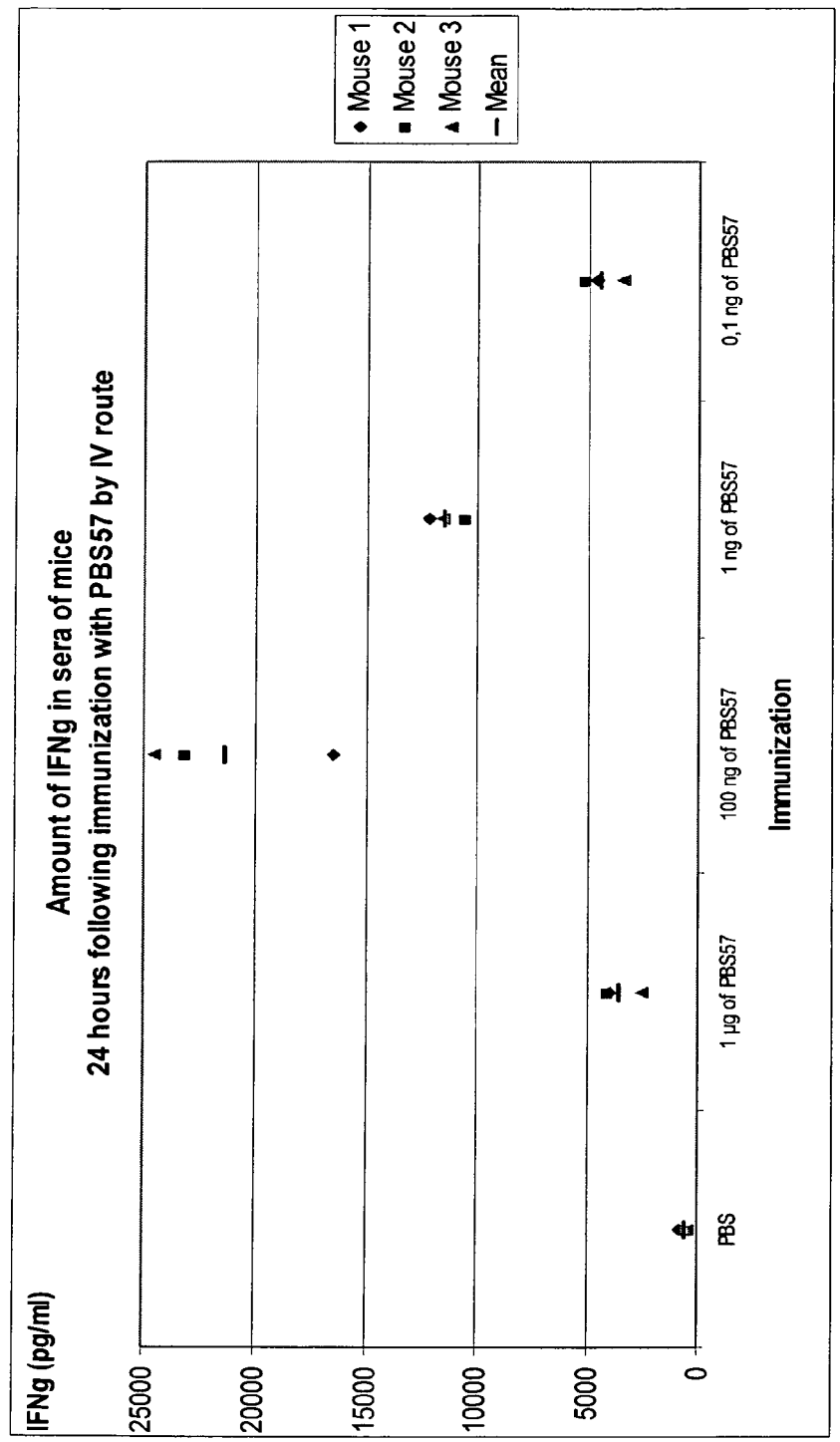
FIG. 4A is a graph depicting accumulation of IFNγ in sera of mice 24 hours after inoculation with varying concentrations of PBS-57.
Figure 4B:
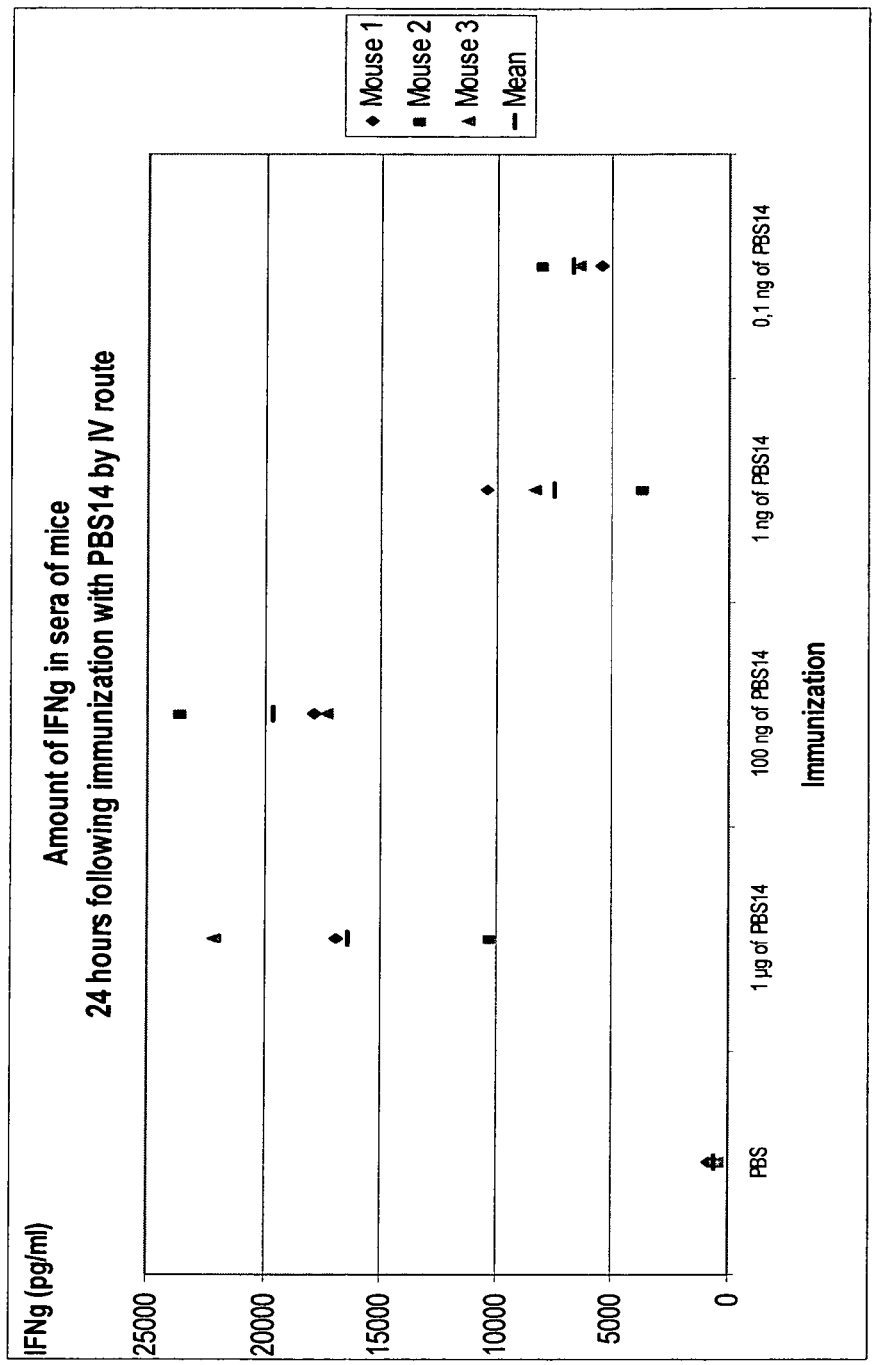
FIG. 4B is a graph depicting accumulation of IFNγ in sera of mice 24 hours after inoculation with varying concentrations of PBS-14.
Figure 4C:
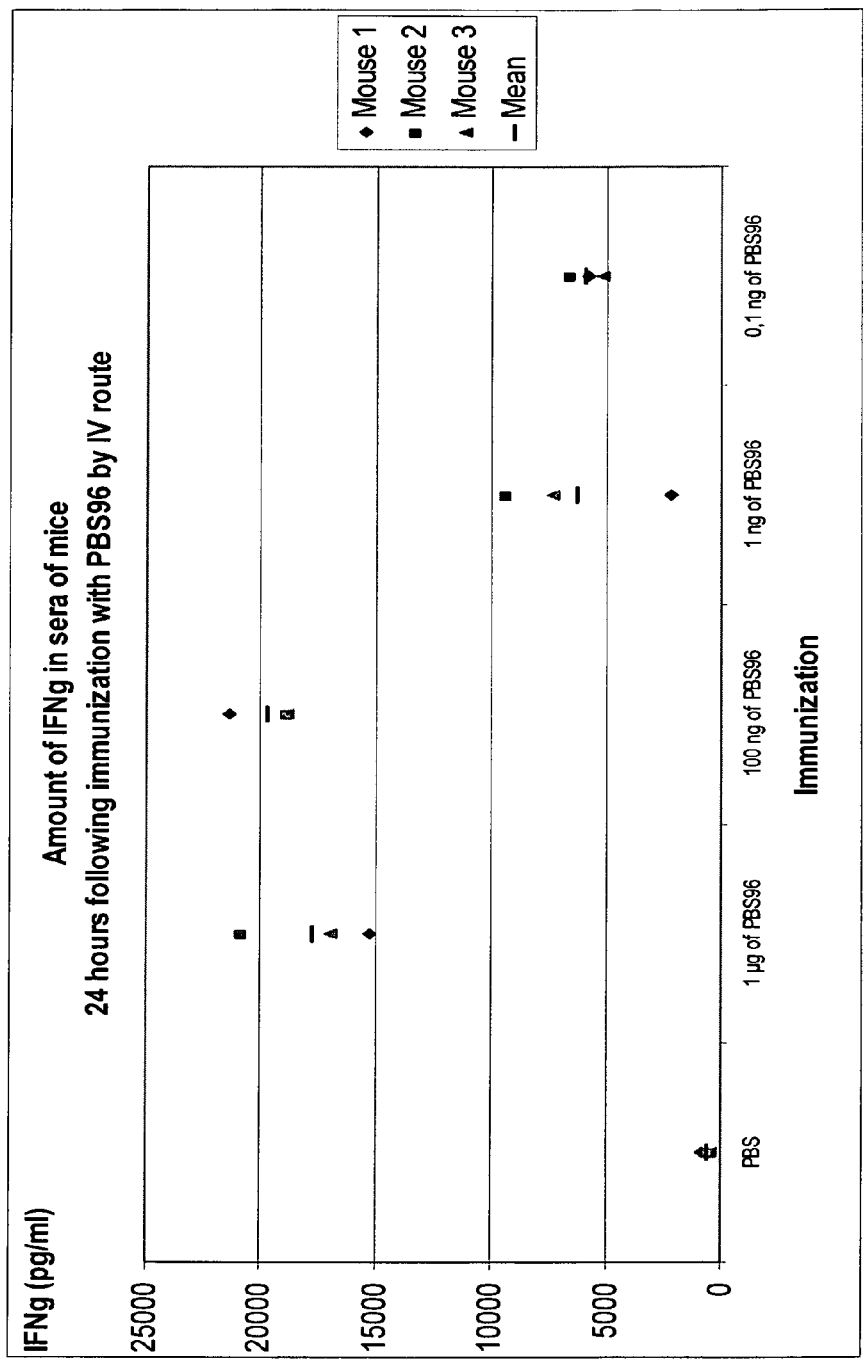
FIG. 4C is a graph depicting accumulation of IFNγ in sera of mice 24 hours after inoculation with varying concentrations of PBS-96.
Figure 4D:
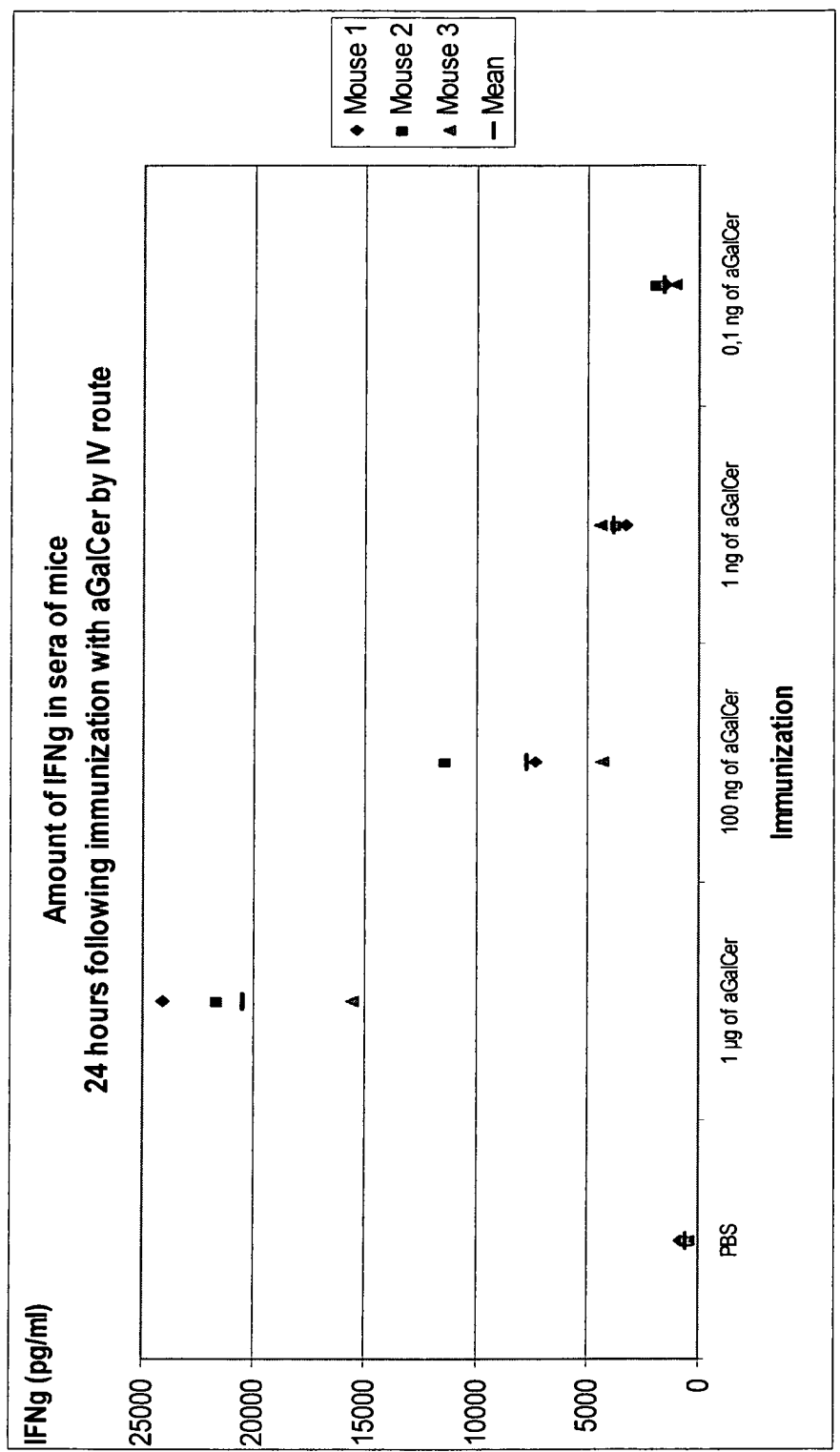
FIG. 4D is a graph depicting accumulation of IFNγ in sera of mice 24 hours after inoculation with varying concentrations of αGalCer.

Results are expressed as IFNγ concentration (pg/ml) in sera and take into account the dilution factor. FIG. 4 depicts results using the Quantikine mouse IFNγ kit by RD systems. FIG. 4A depicts results of IFNγ levels for mice immunized with PBS-57, FIG. 4B depicts results of IFNγ levels for mice immunized with PBS-14, FIG. 4C depicts results of IFNγ levels for mice immunized with PBS-96 and FIG. 4D depicts results of IFNγ levels for mice immunized with αGalCer. At 0.1 ng, all adjuvant candidates induce cytokine release, but mice immunized with αGalCer produced three- or four-fold less IFNγ than mice immunized with PBS-57, PBS-14 or PBS-96 (1540.57±397.53 pg/ml, 4398.05±880.86 pg/ml, 6669.31±1231.82 pg/ml, 5823.33±720.69 pg/ml respectively). At 1 ng test adjuvant compound, PBS-57, PBS-14 and PBS-96 (11425.98±833.04 pg/ml, 7481.15±3454.03 pg/ml and 6271.95±3737.53 pg/ml, averaged, respectively) showed a larger response than αGalCer (average of 3802.99±586.02 pg/ml). At 100 ng of test adjuvant compound, PBS-57, PBS-96 and PBS-14 all produced higher IFNγ levels than αGalCer (21432.76±4312.76 pg/ml for PBS-57, 19679.89±1443.48 pg/ml for PBS-96, 19582.18±3421.20 pg/ml for PBS-14, and 7714.37±3529.07 pg/ml for αGalCer, averaged). At 1 μg test compound, PBS-57 showed a weaker response (3353.45±867.57 pg/ml) compared to the dose of 100 ng (21432.76±4312.76 pg/ml) while PBS-14 or PBS-96 still showed a lower but still robust response (16392.53±5957.70 pg/ml and 17720.11±2869.97 pg/ml respectively) than at the dose of 100 ng (19582.18±3421.20 pg/ml and 19679.89±1443.48 pg/ml respectively).

Figure 5:
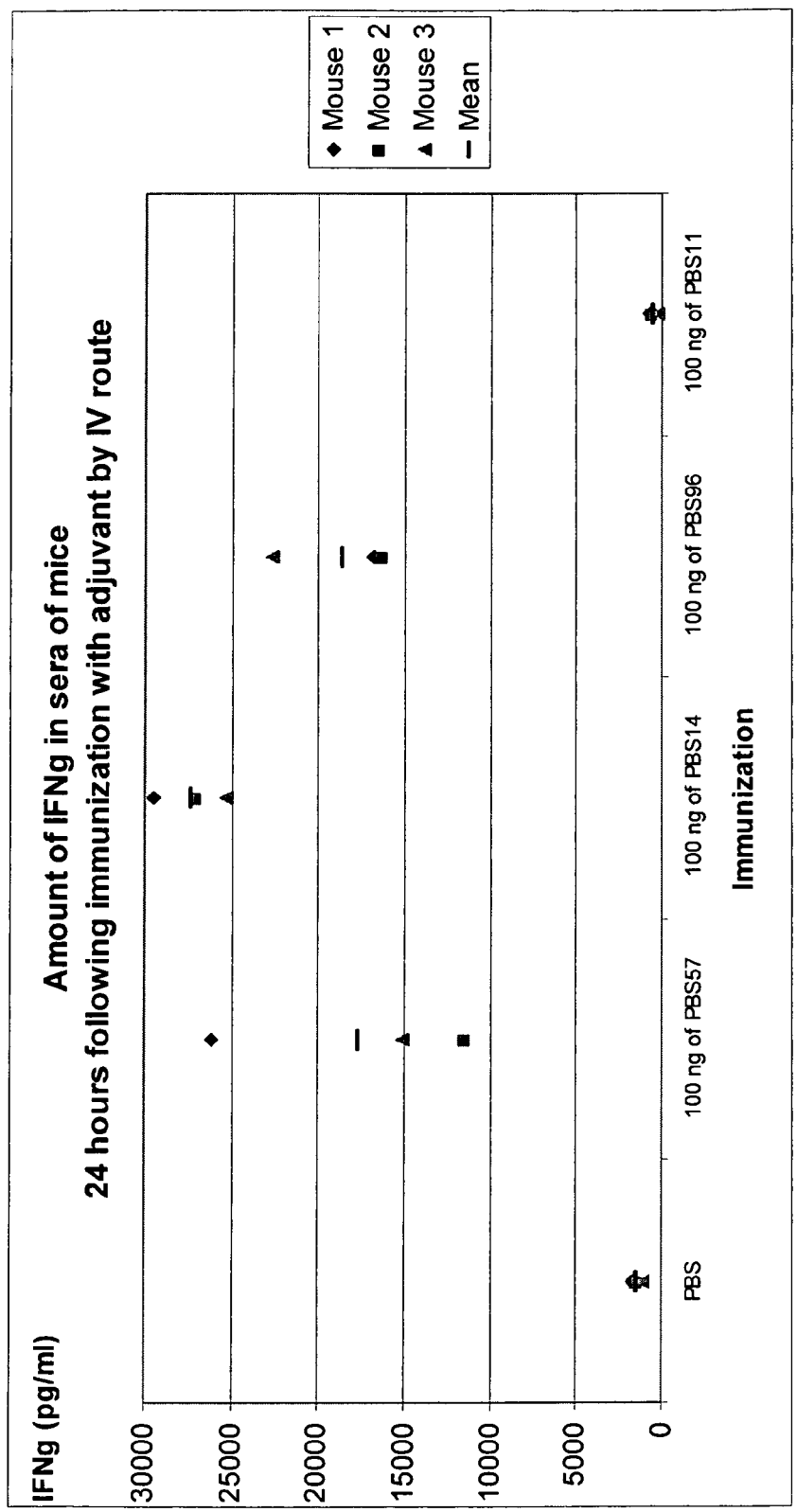
FIG. 5 is a graph comparing accumulation of IFNγ in the sera of mice 24 hours after inoculation with 100 ng of PBS-57, PBS-96, PBS-14 or PBS-11.

Another set of mice were used to compare the ability of adjuvant compounds to stimulate in vivo cytokine release by the method described above. Five groups of C57BL/6 mice were administered 100 ng of PBS-57, PBS-14, PBS-96, or PBS-11 in 100 μl PBS or 100 μl PBS alone intravenously. The production of IFNγ in sera was measured 24 hours later by ELISA. FIG. 5 depicts results for mice immunized with 100 ng of PBS-11, PBS-96, PBS-14 and PBS-57.

Overall, administration of PBS-14 and PBS-96 give a similar IFNγ response to PBS-57, and an unexpectedly greater response than administration of PBS-11.

Example 4

Comparison of the Enhancement of the CD8+ T Cell Response by PBS-96, PBS-14, PBS-11, and PBS-57

Figure 6:
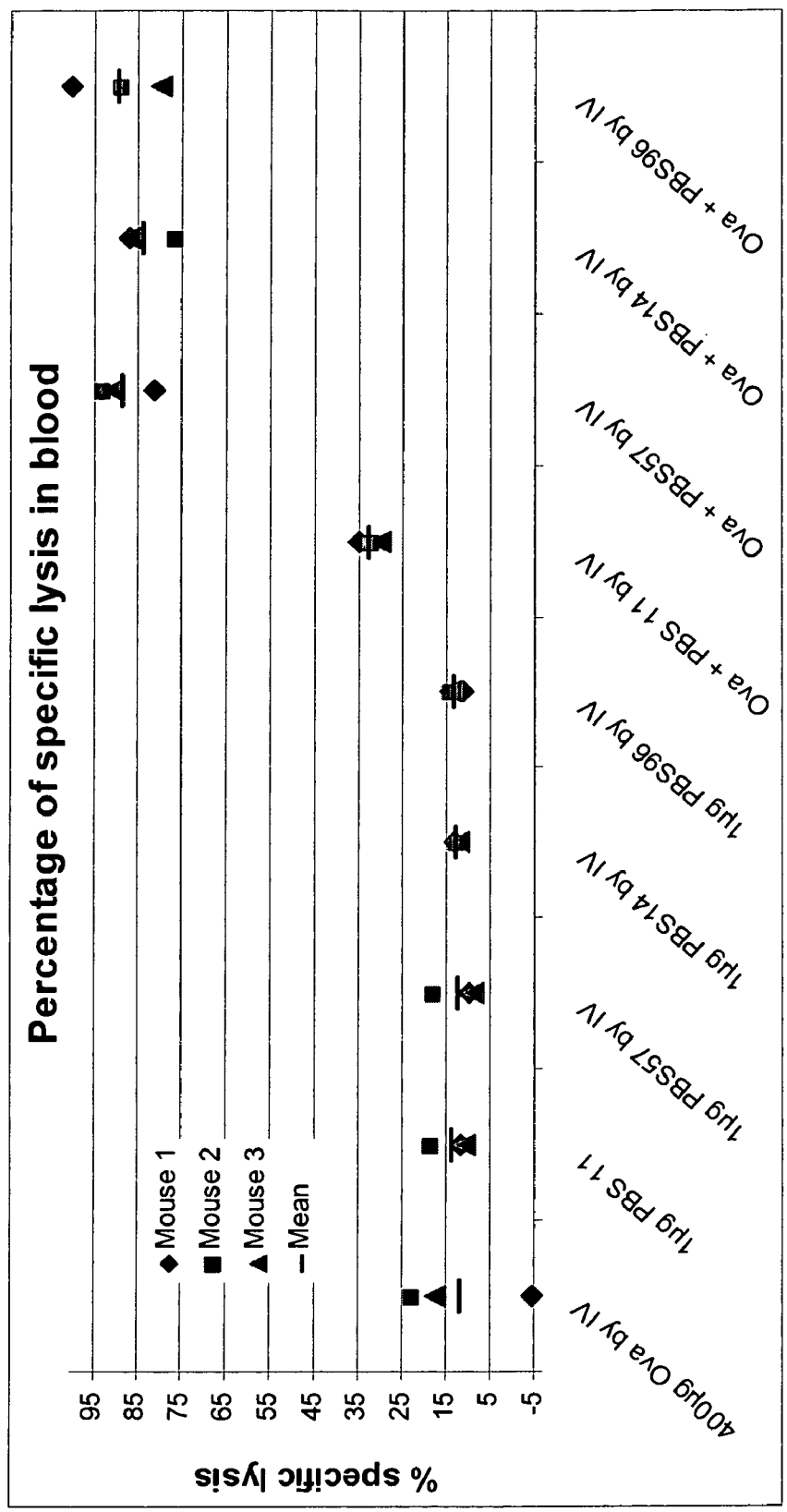
FIG. 6 is a graph depicting specific lysis of Ova-specific target cells in the blood of mice injected IV with PBS-11, PBS-57, PBS-96 or PBS-14, with or without Ova.

To determine the ability of the test adjuvant compounds to induce in vivo specific cytotoxic T cell response (CD8+) in combination with antigen, the test compounds were tested by the method described in Example 1. Nine groups of mice where immunized on day 0 intravenously (IV) as follows:
Group 1: 400 μg of Ova into 100 μl of PBS;
Group 2: 1 μg of PBS-11 into 100 μl of PBS;
Group 3: 1 μg of PBS-57 new formulation into 100 μl of PBS;
Group 4: 1 μg of PBS-14 into 100 μl of PBS;
Group 5: 1 μg of PBS-96 into 100 μl of PBS;
Group 6: 400 μg of Ova+1 μg of PBS-11 into 100 μl of PBS;
Group 7: 400 μg of Ova+1 μg of PBS-57 new formulation into 100 μl of PBS;
Group 8: 400 μg of Ova+1 μg of PBS-14 into 100 μl of PBS;
Group 9: 400 μg of Ova+1 μg of PBS-96 into 100 μl of PBS.
Target cells were mixed with a final ratio of 50/50 of low concentration CFSE loaded cells to high concentration CFSE loaded cells ($1 \times 10^7$ cells each concentration, $2 \times 10^7$ cells total per 100 μl) and injected intravenously into each of the immunized mice on day 10. On day 11, mice were sacrificed and blood samples were collected from the orbital sinus. Specific cell lysis of the Ova-specific target cells was monitored by flow cytometry of the peripheral blood cells. Specific cell lysis was determined as described above. Results are shown in FIG. 6. The average Ova-specific cell lysis was 11.8±14.4% for mice treated with Ova alone, 32.3±2.5% for mice treated with Ova and PBS-11, 88.1±6.2% in mice treated with Ova and PBS-57, 83.3±6.1% for mice treated with Ova and PBS-14, and 89.2±10.3% in mice treated with Ova and PBS-96. These results demonstrate that PBS-14 and PBS-96 are as effective as PBS-57 at inducing an in vivo cytotoxic response after intravenous administration in combination with antigen.

Example 5

Figure 7:
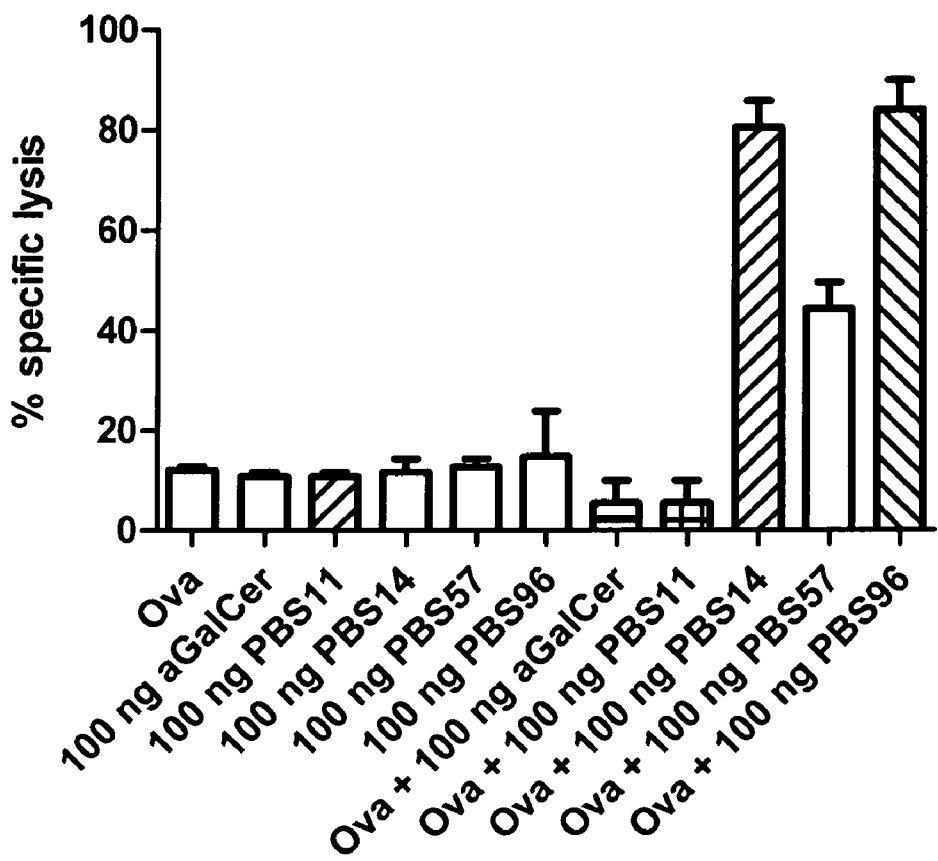
FIG. 7 is a graph showing specific lysis of OVA-specific target cells in mice injected IM with 100 ng of the indicated adjuvant, with or without OVA.
Figure 8:
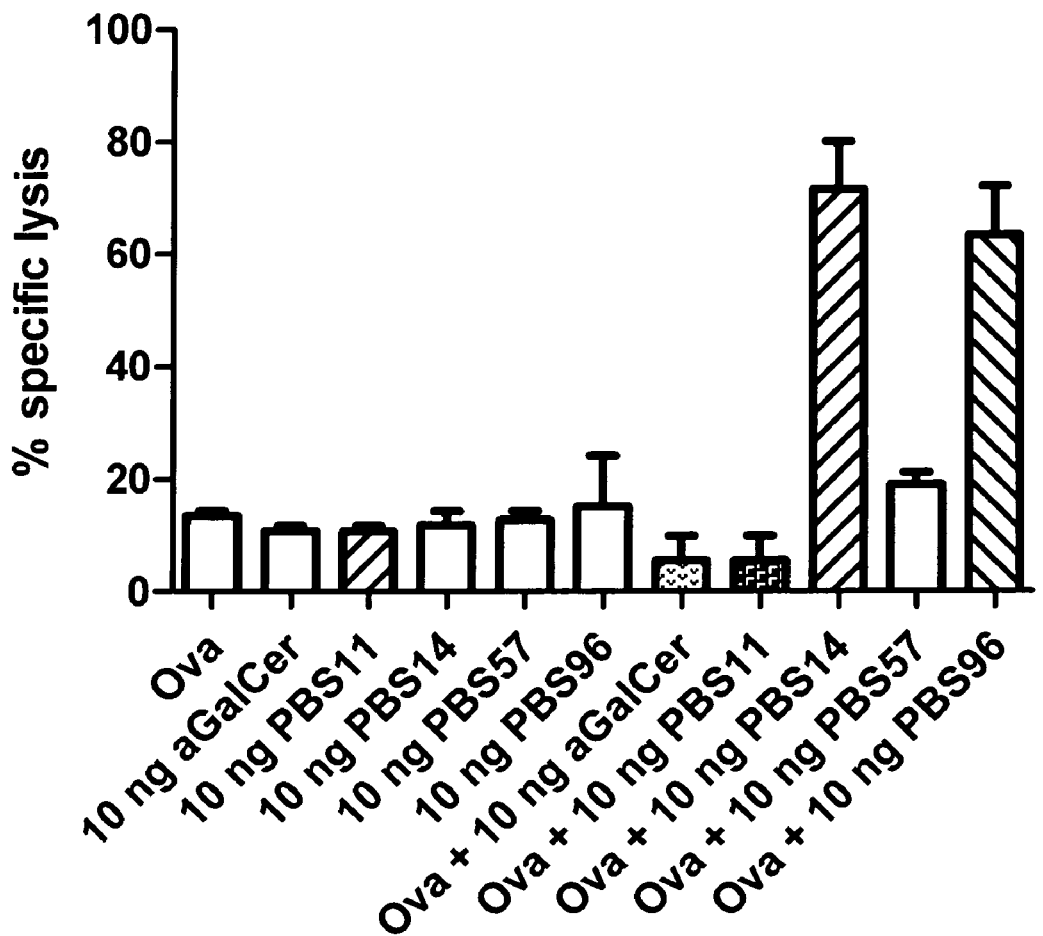
FIG. 8 is a graph showing specific lysis of OVA-specific target cells in mice injected IM with 10 ng of the indicated adjuvant, with or without OVA.

Comparison of the Enhancement of the CD8+ T Cell Response by Decreasing Amounts of Adjuvant after Intramuscular Injection To determine the relative ability of the test adjuvant compounds to enhance the immune response, a similar experiment to that described in Example 2 was performed. In this experiment mice were injected intravenously with decreasing amounts of adjuvant (100 ng and 10 ng, respectively) in combination with 50 μg of OVA antigen at day 0 as follows:
Experiment A:
Group 1: 50 μg of Ova into 100 μl PBS
Group 2: 100 ng αGalCer;
Group 3: 100 ng PBS-11
Group 4: 100 ng PBS-14
Group 5: 100 ng PBS-57
Group 6: 100 ng PBS-96
Group 7: 50 μg of Ova with 100 ng αGalCer;
Group 8: 50 μg of Ova with 100 ng PBS-11
Group 9: 50 μg of Ova with 100 ng PBS-14
Group 10: 50 μg of Ova with 100 ng PBS-57
Group 11: 50 μg of Ova with 100 ng PBS-96
Experiment B:
Group 1: 50 μg of Ova into 100 μl PBS
Group 2: 10 ng αGalCer;
Group 3: 10 ng PBS-11
Group 4: 10 ng PBS-14
Group 5: 10 ng PBS-57
Group 6: 10 ng PBS-96
Group 7: 50 μg of Ova with 10 ng αGalCer;
Group 8: 50 μg of Ova with 10 ng PBS-11
Group 9: 50 pig of Ova with 10 ng PBS-14
Group 10: 50 μg of Ova with 10 ng PBS-57
Group 11: 50 μg of Ova with 10 ng PBS-96
Target cells were administered on day 10 of the experiment and blood was collected on day 11. The results for Experiment A using 100 ng of each adjuvant are shown in FIG. 7 and the results for Experiment B are shown in FIG. 8. FIGS. 7 and 8 demonstrate that PBS-14 and PBS-96 are unexpectedly better than other adjuvants at enhancing the CD8+ T cell response to an antigen at low doses when administered intramuscularly. In fact after administration of OVA and only 10 ng of either PBS-14 or PBS-96 intramuscularly the percentage of specific lysis of the target cells by CD8+ T cells is still over 60%, while the percentage of specific lysis of target cells after administration of OVA and the same amount of PBS-57, PBS-11 or αGalCer was indistinguishable from the controls.

Example 6

Comparison of the Enhancement of the CD8+ T Cell Response by Decreasing Amounts of Adjuvant after Intramuscular Injection To verify the results obtained using the in vivo cytotoxicity assay described in the Examples above, similar experiments were performed and CD8+ T cell activation was determined by measuring the percentage of OVA-specific CD8+ T cells using a pentamer assay. Briefly, mice were injected intramuscularly with the indicated amounts of OVA and test adjuvant compound at either 1 μg or 100 ng per mouse, respectively on day 0 as follows:

Experiment A:
Group 1: 100 μl of PBS;
Group 2: 50 μg of Ova into 100 μl PBS;
Group 3: 50 μg of Ova with 1 μg αGalCer;
Group 4: 50 μg of Ova with 1 μg PBS-11
Group 5: 50 μg of Ova with 1 μg PBS-14
Group 6: 50 μg of Ova with 1 pig PBS-57
Group 7: 50 μg of Ova with 1 μg PBS-96
Experiment B:
Group 1: 100 μl of PBS;
Group 2: 50 μg of Ova into 100 μl PBS;
Group 3: 50 μg of Ova with 100 ng αGalCer;
Group 4: 50 μg of Ova with 100 ng PBS-11
Group 5: 50 μg of Ova with 100 ng PBS-14
Group 6: 50 μg of Ova with 100 ng PBS-57
Group 7: 50 as of Ova with 100 ng PBS-96

Figure 9:
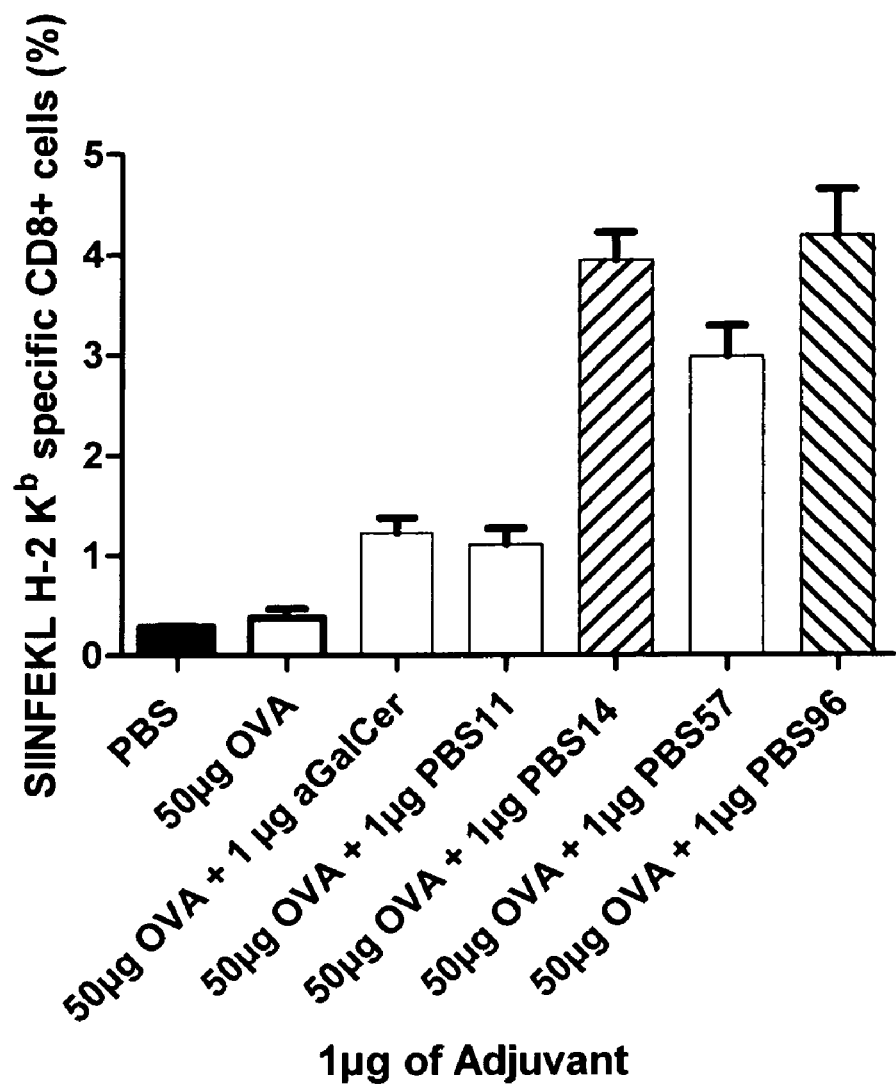
FIG. 9 is a graph showing percentages of CD8+ T cells responsive to the SIINFEKL pentamer in mice injected IM with 1 μg of the indicated adjuvant, with or without OVA.
Figure 10:
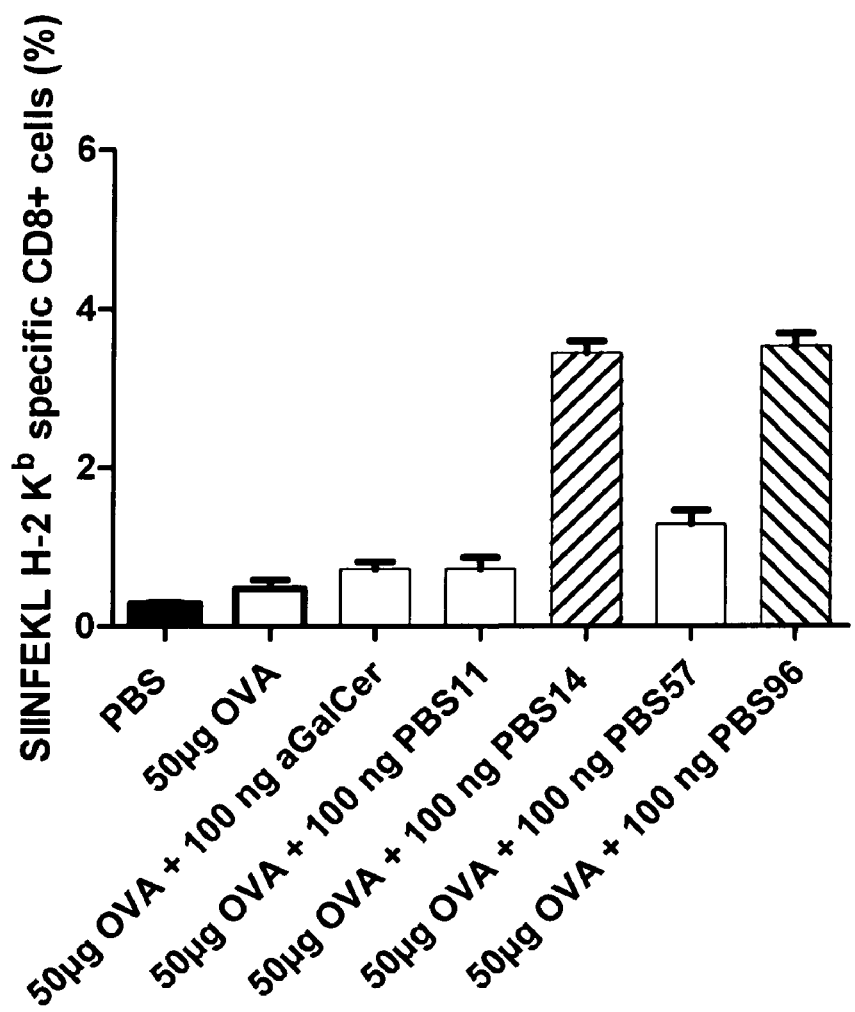
FIG. 10 is a graph showing percentages of CD8+ T cells responsive to the SIINFEKL pentamer in mice injected IM with 100 ng of the indicated adjuvant, with or without OVA.

A second injection was administered to the mice on day 14 and blood was collected from the mice on day 21. The lymphocytes were collected and analyzed by FACS analysis using H-2K$^b$ SIINFEKL pentamer and CD8 antibody to detect CD8+ T cells responsive to OVA. The results of Experiment A are shown in FIG. 9 and the results of Experiment B are shown in FIG. 10. FIG. 9 demonstrates that when administered at 1 μg PBS-14, PBS-96 and PBS-57 enhanced the percentage of OVA specific CD8+ T cells after vaccination, while PBS-11 and αGalCer were not as effective. FIG. 10 demonstrates that at the lower dose of 100 ng PBS-14 and PBS-96 were surprisingly much better at enhancing the CD8+ T cell response to an antigen as compared to PBS-57, PBS-11 and αGalCer.

Example 7

Comparison of the Enhancement of the Humoral Response Following Intramuscular Immunization with Adjuvant and Antigen To evaluate whether the humoral and CD4+ T helper cell immune responses were also enhanced by administration of the test adjuvants with antigen, the IgG1 and IgG2a antibody responses were measured in mice vaccinated with OVA with or without the test adjuvants. Mice (6 per group) were injected intramuscularly with 50 μg of OVA either alone or in combination with 100 ng of the indicated adjuvants (Freund's adjuvant was used as a positive control) as follows:

Group 1: 500 μg of Ova with CFA/IFA (Positive control)
Group 2: 50 μg of Ova
Group 3: 50 μg of Ova and 100 ng of αGalCer
Group 4: 50 μg of Ova and 100 ng of PBS-11
Group 5: 50 μg of Ova and 100 ng of PBS-14
Group 6: 50 μg of Ova and 100 ng of PBS-57
Group 7: 50 μg of Ova and 100 ng of PBS-96

Figure 11:
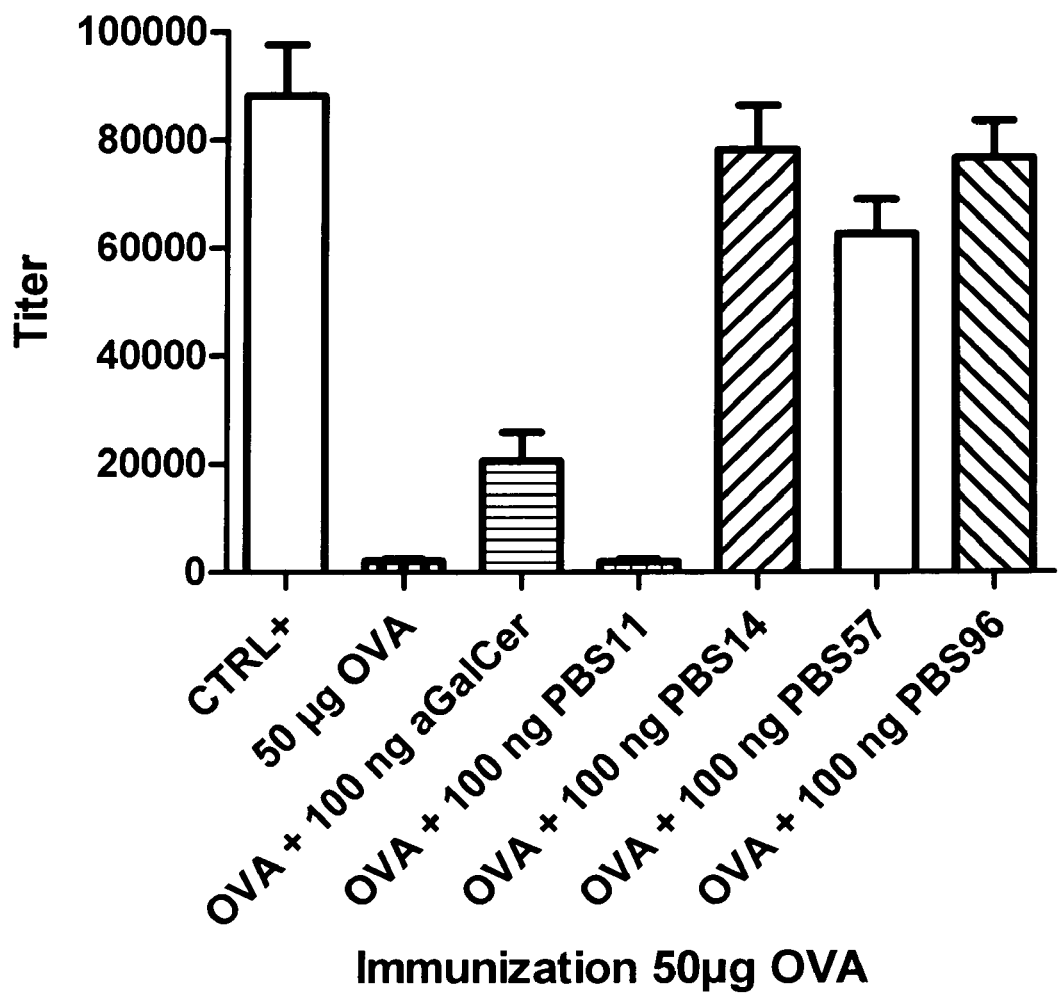
FIG. 11 is a graph showing titers of IgG1 in the blood of mice injected IM with 100 ng of the indicated adjuvant, with or without OVA.
Figure 12:
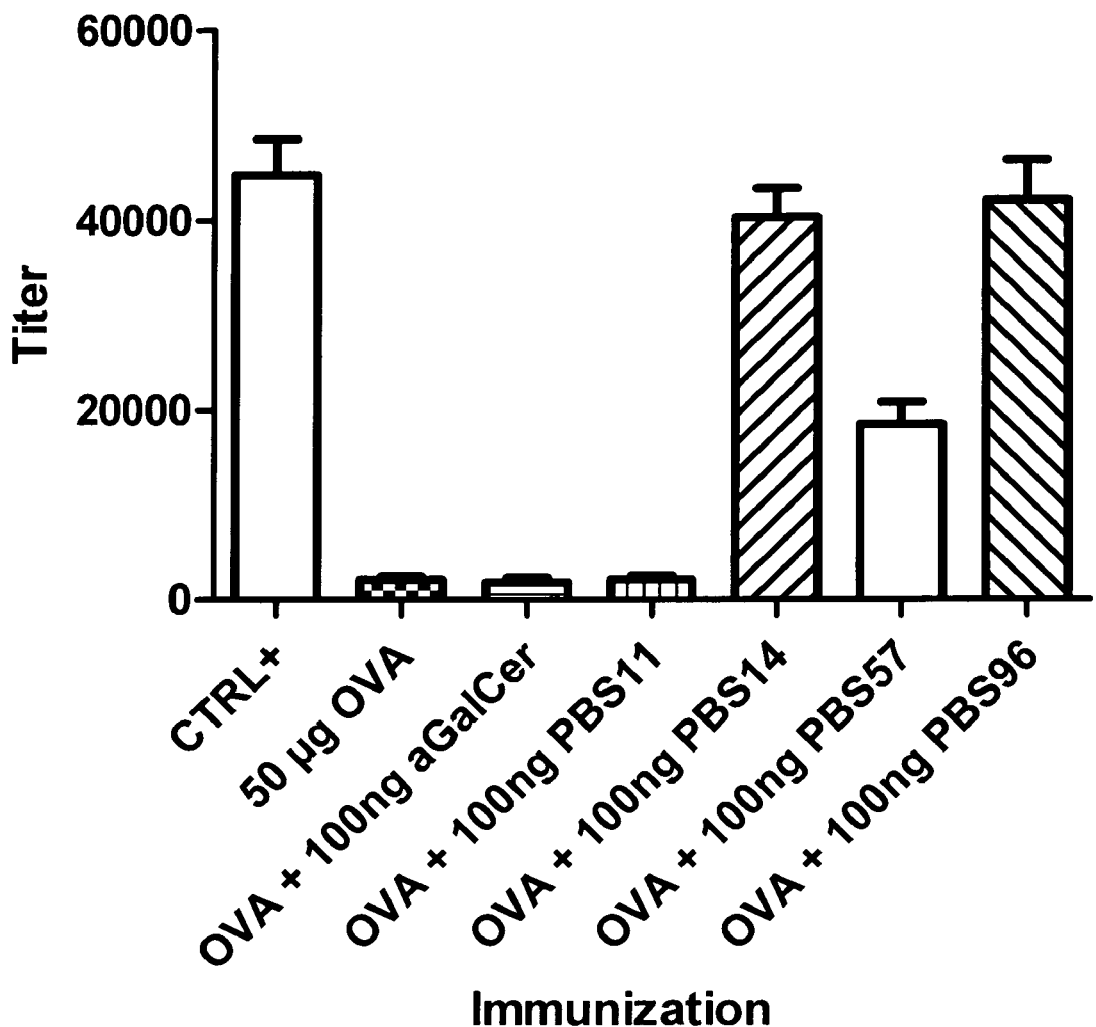
FIG. 12 is a graph showing titers of IgG2a in the blood of mice injected IM with 100 ng of the indicated adjuvant, with or without OVA.

At 14 days post-injection, blood samples were collected and ELISAs for IgG1 and IgG2a were performed using mouse monoclonal antibodies specific for OVA isotype IgG1 or IgG2a. The results are shown as the titer of the antibody in peripheral blood in ng/ml. The results for IgG1 are depicted in FIG. 11 and those for IgG2a are depicted in FIG. 12. As shown in FIG. 11, PBS-14, PBS-96 and PBS-57 were all able to elicit a robust IgG1 titer and enhanced the OVA-specific IgG1 titer as compared to vaccination with OVA alone or OVA in combination with PBS-11 or αGalCer. Surprisingly, PBS-14 and PBS-96 enhanced the OVA specific IgG2a titer about as well as Freund's adjuvant and much better than PBS-57.

While the compositions and methods of this invention have been described in terms of exemplary embodiments, it will be apparent to those skilled in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention. In addition, all patents and publications listed or described herein are incorporated in their entirety by reference.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application.

I claim:

1. A method of enhancing an immune response of a subject to an antigen comprising administering an antigen and a composition comprising a compound of formula I:

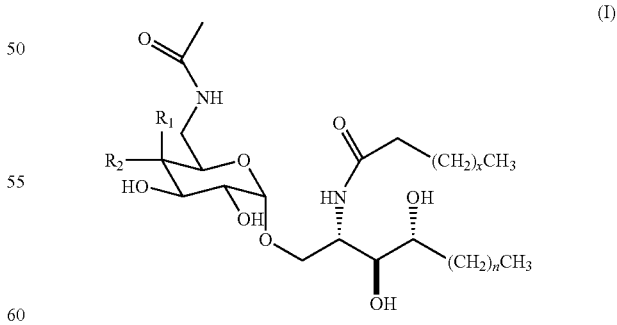

wherein $R_1$ is H or —OH, $R_2$ is —H or —OH, x is an integer from 18 to 26, and n is an integer from 10 to 15, to the subject, wherein the immune response of the subject to the antigen is enhanced relative to an immune response of a control to the antigen.

2. The method of claim 1, wherein x is 23.

3. The method of claim 1, wherein x is 21.

4. The method of claim 1, wherein n is 13.

5. The method of claim 1, wherein the antigen and the composition are administered to the subject intramuscularly.

6. The method of claim 1, wherein the immune response of the subject is enhanced at least 50% relative to the control.

7. The method of claim 1, wherein the immune response of the subject is enhanced at least 100% relative to the control.

8. Then method of claim 1, wherein the immune response of the subject is enhanced at least 1000% relative to the control.

9. The method of claim 1, wherein the antigen and the composition are administered concurrently.

10. The method of claim 1, wherein the composition is administered via a route selected from the group consisting of intravenously, intramuscularly, subcutaneously, intradermally, intraperitoneally, intranasally and by inhalation.

11. The method of claim 1, wherein the enhanced immune response is a humoral immune response of the subject to the antigen, wherein the humoral immune response of the subject to the antigen is enhanced relative to an immune response of a control to the antigen.

12. The method of claim 11, wherein the humoral immune response comprises production of IgG antibodies.

13. The method of claim 11, wherein the humoral immune response comprises production of IgA antibodies.

14. The method of claim 1, wherein the enhanced immune response is a CD4+ T cell response of the subject to the antigen, wherein the immune response of the subject to the antigen is enhanced relative to a CD4+ T cell response of a control to the antigen.

15. The method of claim 14, wherein the enhanced CD4+ T cell response comprises activation of CD4+ T lymphocytes.

16. The method of claim 15, wherein activation of the CD4+ T lymphocytes comprises an increase in a ThI immune response.

17. The method of claim 15, wherein activation of the CD4+ T lymphocytes comprises an increase in a Th2 immune response.

18. The method of claim 15, wherein activation of the CD4+ T lymphocytes comprises an increase in both a ThI and a Th2 immune response.

19. The method of claim 1, wherein the enhanced immune response is a CD8+ T cell response of the subject to the antigen, wherein the immune response of the subject to the antigen is enhanced relative to a CD8+ T cell response of a control to the antigen.

20. The method of claim 19, wherein the enhanced CD8+ T cell response comprises activation of the CD8+ T lymphocytes.

21. The method of claim 20, wherein the activation of the CD8+ T lymphocytes comprises an increase in cytotoxic response.

22. The method of claim 1, wherein the enhanced immune response is activation of antigen presenting cells of the subject to the antigen, wherein the immune response of the subject to the antigen is enhanced relative to activation of antigen presenting cells of a control to the antigen.

23. The method of claim 5, wherein the immune response of the subject is enhanced at least 50% relative to the control.

24. The method of claim 5, wherein the immune response of the subject is enhanced at least 100% relative to the control.

25. The method of claim 5, wherein the immune response of the subject is enhanced at least 1000% relative to the control.

26. The method of claim 1, wherein the antigen and the composition are administered concurrently.

27. The method of claim 1, wherein the composition is administered via a route selected from the group consisting of intravenously, intramuscularly, subcutaneously, intradermally, intraperitoneally, intranasally and by inhalation.

* * * * *